(12) United States Patent
Shahar et al.

(10) Patent No.: US 7,663,111 B2
(45) Date of Patent: Feb. 16, 2010

(54) VARIABLE COLLIMATION IN RADIATION DETECTION

(75) Inventors: Arie Shahar, Moshav Magshimim (IL); Uri El-Hanany, Rehovot (IL); Eliezer Traub, Ramat Gan (IL); Zeev Gutman, Kfar Mordechi (IL); Alexander Cherlin, Rishon Le-Zion (IL)

(73) Assignee: Orbotech Ltd., Yavne (IL)

( * ) Notice: Subject to any disclaimer, the term of this patent is extended or adjusted under 35 U.S.C. 154(b) by 166 days.

(21) Appl. No.: 11/729,140

(22) Filed: Mar. 28, 2007

(65) Prior Publication Data

US 2008/0237482 A1    Oct. 2, 2008

(51) Int. Cl.
*G21K 1/02* (2006.01)
(52) U.S. Cl. ............ 250/363.1; 378/147; 378/150
(58) Field of Classification Search ............ 378/150, 378/147
See application file for complete search history.

(56) References Cited

U.S. PATENT DOCUMENTS

| | | | |
|---|---|---|---|
| 4,118,632 A * | 10/1978 | Luig | 250/363.1 |
| 4,302,675 A * | 11/1981 | Wake et al. | 250/363.04 |
| 4,446,570 A * | 5/1984 | Guth | 378/149 |
| 4,584,478 A * | 4/1986 | Genna et al. | 250/363.04 |
| 4,859,852 A * | 8/1989 | Genna et al. | 250/363.1 |
| 5,847,398 A | 12/1998 | Shahar et al. | |
| 6,061,426 A * | 5/2000 | Linders et al. | 378/149 |
| 6,201,852 B1 * | 3/2001 | Goddu et al. | 378/159 |
| 6,353,227 B1 * | 3/2002 | Boxen | 250/363.1 |
| 6,762,413 B2 * | 7/2004 | Zeng | 250/363.1 |
| 7,015,477 B2 | 3/2006 | Gunter | |
| 7,274,022 B2 * | 9/2007 | Soluri et al. | 250/363.1 |
| 2004/0200965 A1 * | 10/2004 | Umegaki et al. | 250/363.1 |
| 2007/0007454 A1 * | 1/2007 | Stoddart et al. | 250/363.04 |
| 2007/0221853 A1 * | 9/2007 | Joung | 250/363.09 |
| 2007/0248265 A1 * | 10/2007 | Lundstrom et al. | 382/168 |
| 2008/0073540 A1 * | 3/2008 | Vija | 250/363.05 |
| 2008/0073599 A1 | 3/2008 | Vija | |

OTHER PUBLICATIONS

Gamma and Cosmic Ray Astrophysics Branch, Code 7650—Naval Research Laboratory Washington DC, Nov. 2000.
"A first course in numerical analysis", by Ralston, et al. published by McGraw-Hill, 1977.

* cited by examiner

*Primary Examiner*—David P Porta
*Assistant Examiner*—Yara B Green
(74) *Attorney, Agent, or Firm*—Ladas & Parry LLP

(57) ABSTRACT

Apparatus for detecting radiation emitted from a number of volume elements of a body. The apparatus includes a first plurality of detector elements, each detector element being configured to output signals indicative of an intensity of radiation that is incident thereon. The apparatus also includes a first plurality of adjustable collimator channels, each adjustable collimator channel being associated with and being positioned between a respective detector element and the body, each adjustable collimator channel having a second plurality of dimensional configurations defining respective different sets of the volume elements from which emitted radiation impinges on the respective detector element. A processor computes a radiation intensity from at least a portion of the volume elements in response to the signals output by the detector elements in at least two of the dimensional configurations of the adjustable collimator channels.

34 Claims, 21 Drawing Sheets

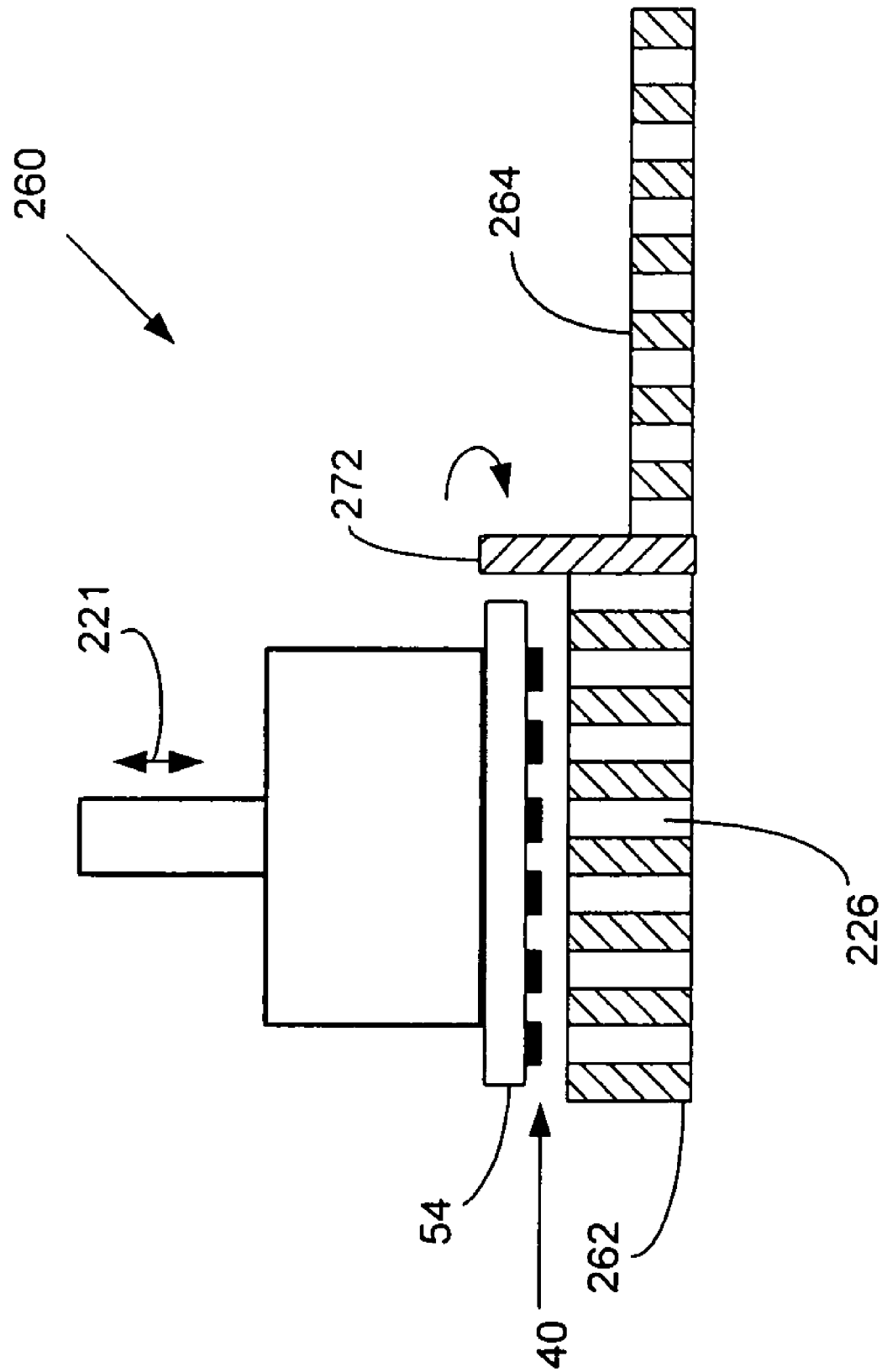

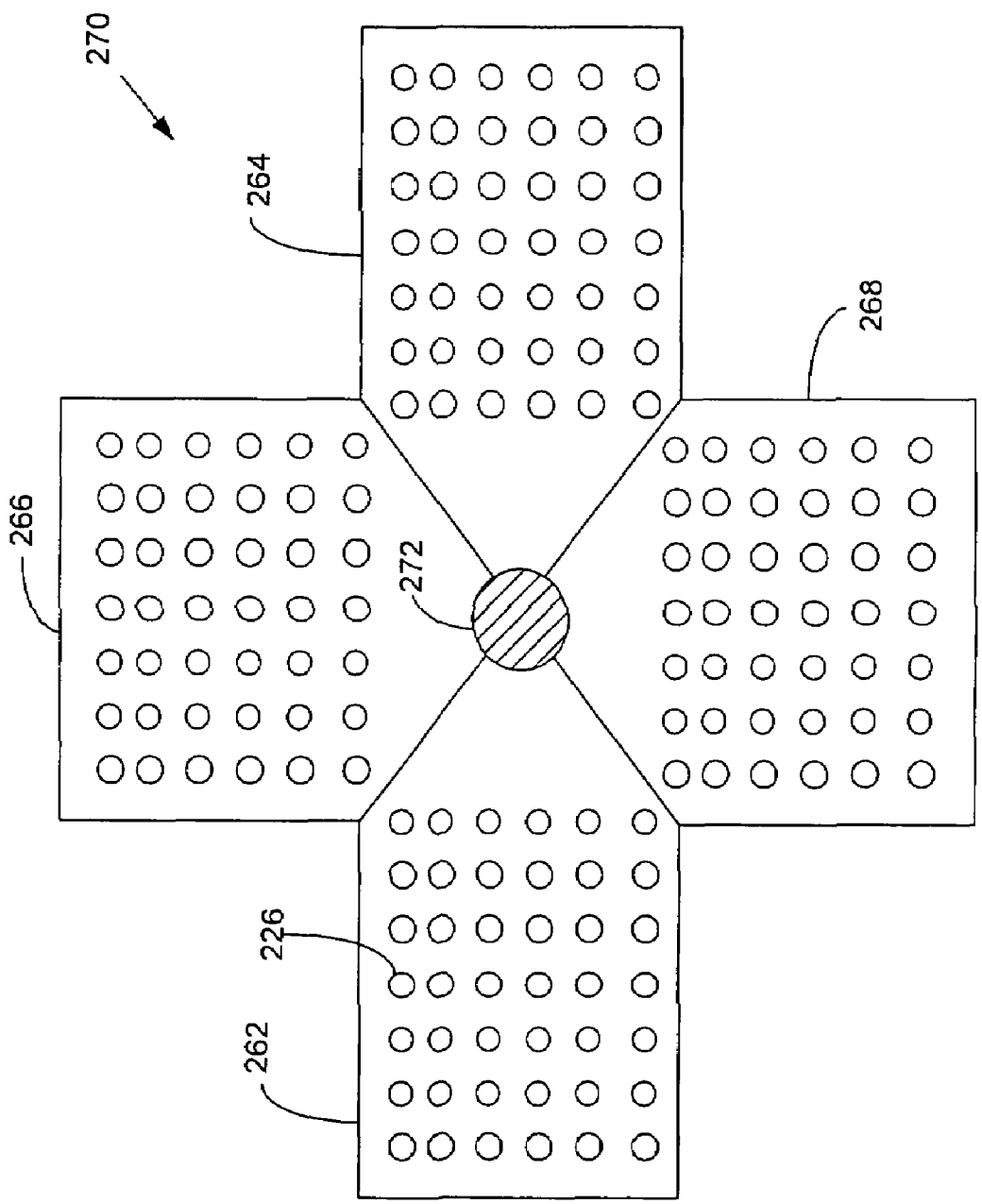

TO REGION 23

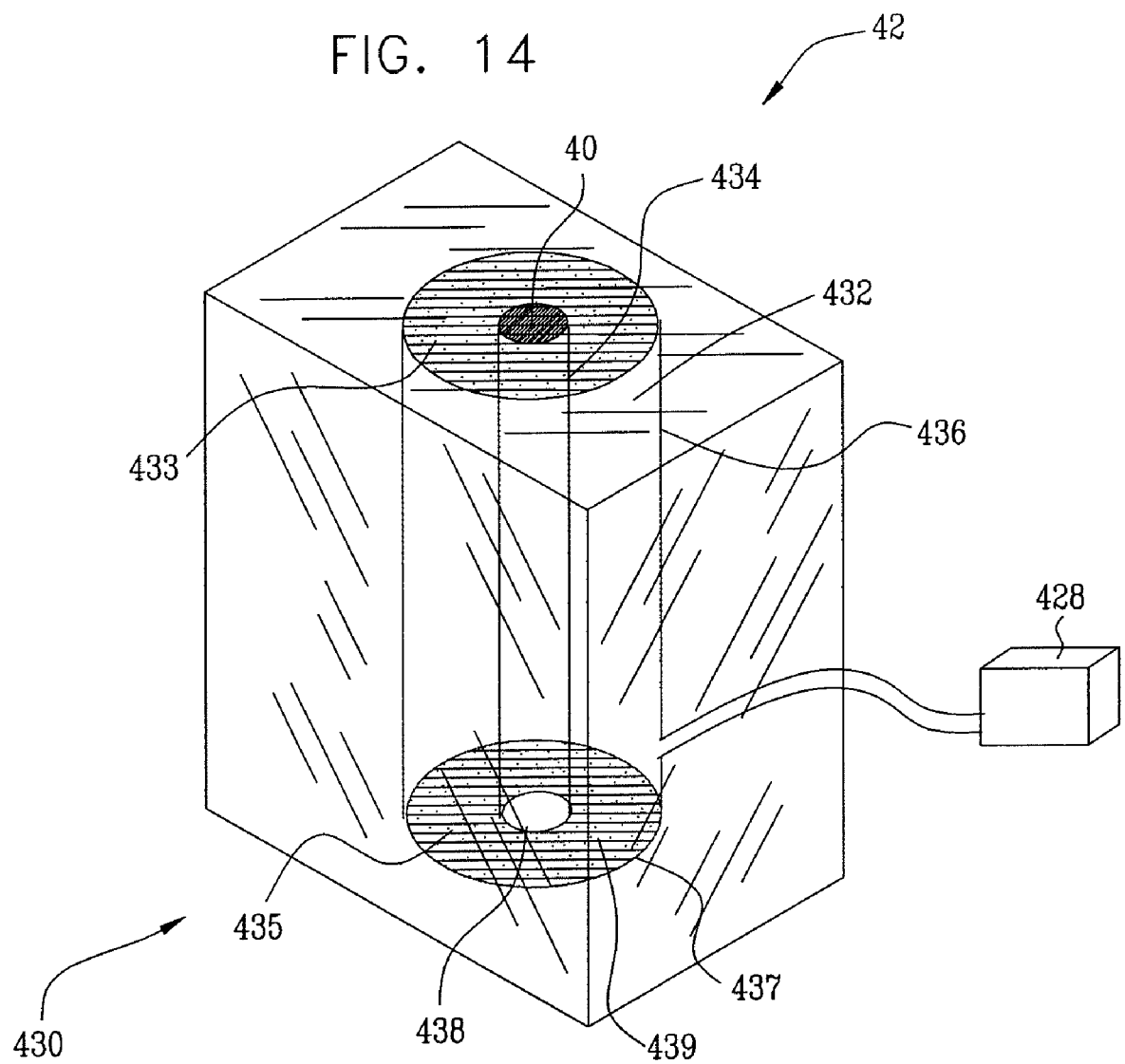

VARIABLE COLLIMATION IN RADIATION DETECTION

FIELD OF THE INVENTION

The present invention relates generally to detection of gamma-ray and X-ray radiation, and specifically to systems and methods of radiation detection for medical diagnosis.

BACKGROUND OF THE INVENTION

In a typical nuclear medicine diagnostic procedure, a radiopharmaceutical material comprising a radioisotope tracer is administered to a patient. An example of a radioisotope tracer is Technetium-99m, which is a gamma ray emitter. Radiation subsequently emitted by the radiopharmaceutical material inside the body indicates sites at which the tracer has been absorbed.

A detector for measuring the emitted radiation is generally positioned at several locations around the body, and a collimator is placed between the body and the detector so that the approximate direction from which radiation is emitted may be determined. The collimator is made of a material that is opaque to gamma-rays and X-rays, such as lead or tungsten. Channels through the collimator allow radiation emitted from a narrow solid angle to pass through the opaque material.

SUMMARY OF THE INVENTION

In an embodiment of the present invention, a collimator comprises a plurality of substantially similar adjustable collimator channels, each collimator channel typically being arranged in a two-dimensional matrix. The collimator is typically positioned, in a camera head, before a detector mounting that provides a detector for each collimator channel. Each collimator channel directs radiation from radioisotopes injected into a region of the body of a patient to its respective detector.

Each collimator channel in the collimator has multiple dimensional configurations. In a given dimensional configuration each collimator channel, collects radiation from a given volume of the region. For each of the multiple configurations the respective multiple volumes for a given channel have a different size. Furthermore, the multiple volumes for each given collimator channel typically enclose each other, in, a manner that is generally similar to Russian nested dolls. The detector for each channel measures respective multiple radiation levels received in the multiple configurations and, as described below, generates one or more images having intensities proportional to the concentration of the radioisotopes and an absorption coefficient in the region. By using collimator channel dimensional configurations that collect radiation from relatively large volumes, embodiments of the present invention reduce the acquisition time required for generation of images representing the region.

The region being imaged may be divided into a number of similarly shaped virtual volume elements, herein termed voxels, each voxel having a respective radioisotope concentration. There is a dependency between the number of adjustable collimator channels, the number of configurations of each channel, and a possible number of voxels. Typically, on the basis of the dependency and the number of configurations, the processor sets the number and size of the voxels, and thus a resolution for the one or more images. Each of the image representations corresponds to a respective set of the voxels, and an operator may select the sets of voxels as desired, for example, as horizontal/vertical plane slices, and/or as one or more non-planar slices.

In some embodiments of the present invention the configurations of a given collimator channel are implemented by changing an effective length and/or a cross-section of the channel.

In a disclosed embodiment, the effective length of a collimator channel is changed by stacking one or more cylinders on each other. Alternatively or additionally, the effective length is changed by changing the separation between two or more cylinders.

In some embodiments, each adjustable collimator channel is configured so that the multiple volumes of the region subtended at a given detector are sections of cones or pyramids having a common vertex and a common axis of symmetry, but different semi-angles.

In one embodiment, at least part of the collimator channel comprises a cavity which can be filled with liquid that is opaque to the radiation. The channel may be adjusted by filling or partly filling the cavity with the liquid, which changes the volume of the region subtended at the detector associated with the collimator channel.

In an alternate embodiment, two or more camera-heads are employed to measure radiation intensity, each camera head having a respective collimator. Each collimator has collimator channels in a different configuration. The camera heads are mounted so that they, and the detectors they contain, can be repositioned sequentially to the same position with respect to the region of the patient's body, and radiation measurements are made for each camera head. When a given camera head is in the position, a processor operates the camera. The signals received from the different camera heads (each in the same position) correspond to the signals received by one camera head having adjustable collimator channels.

In a further alternate embodiment, rather than the two or more complete camera heads being repositioned, only the collimators are repositioned, the camera heads and the detectors they contain remaining fixed in position. In a yet further alternate embodiment, at least one of the collimators of the two or more camera heads comprises collimator channels that have multiple dimensional configurations.

There is therefore provided, according to an embodiment of the present invention, apparatus for detecting radiation emitted from a number of volume elements of a body, the apparatus including:

a first plurality of detector elements, each detector element being configured to output signals indicative of an intensity of radiation that is incident thereon;

a first plurality of adjustable collimator channels, each adjustable collimator channel being associated with and being positioned between a respective detector element and the body, each adjustable collimator channel having a second plurality of dimensional configurations defining respective different sets of the volume-elements from which emitted radiation impinges on the respective detector element; and a processor coupled to compute a radiation intensity from at least a portion of the volume elements in response to the signals output by the detector elements in at least two of the dimensional configurations of the adjustable collimator channels.

Each adjustable collimator channel may include a first collimator channel aligned with a second collimator channel and separated therefrom by an adjustable gap. The first collimator channel may be aligned with the respective detector element and may be separated therefrom by a variable gap. Typically, the processor is coupled to adjust at least one of the variable gap and the adjustable gap. The first and second collimator channels may have different cross-sectional areas.

In one embodiment, each adjustable collimator channel includes a third plurality of collimator channels, and the processor is coupled to align one or more of the third plurality of collimator channels with the respective detector element.

Alternatively, each adjustable collimator channel includes a third plurality of collimator channels each having different lengths.

In a disclosed embodiment each adjustable collimator channel includes a cavity which is configured to receive a liquid opaque to the radiation. The liquid may include mercury. The cavity may alter a length of the adjustable collimator channel on receipt of the liquid. Alternatively, the cavity alters a cross-section of the adjustable collimator channel on receipt of the liquid.

Typically, the emitted radiation includes gamma rays.

The processor may be configured to generate a representation of radioisotopes in the body in response to the radiation intensity.

In some embodiments, the dimensional configurations include a first configuration defining a first set of the volume elements and a second configuration defining a second set of the volume elements, wherein the first set includes the second set. Typically, the first set includes a first section of a first cone, and the second set includes a second section of a second cone, the first and the second cones having a common axis of symmetry.

The processor may be coupled to compute the number of the volume elements in response to the value of the first plurality, the value of the second plurality, and the signals. Typically, the processor may be coupled to compute the number of the volume elements iteratively, so as to determine a largest number of the volume elements. The number may be a product of the value of the first plurality and the value of the second plurality.

The portion may include a group of the volume elements selected by an operator of the apparatus.

There is further provided, according to an embodiment of the present invention, apparatus for detecting radiation emitted from a body, the apparatus including:

a first camera head, including a first detector element and a first collimator channel, the first detector element operative to output first signals indicative of a first radiation intensity, the first collimator channel being positioned between the first detector element and the body so as to define a first volume of the body from which emitted radiation impinges on the first detector element;

a second camera head, including a second detector element and a second collimator channel, the second detector element operative to output second signals indicative of a second radiation intensity, the second collimator channel being positioned between the second detector element and the body so as to define a second volume of the body from which emitted radiation impinges on the detector element, the second volume being smaller than and included in the first volume; and a processor coupled to compute a radiation intensity from at least a portion of the body in response to the first signals and the second signals.

The apparatus may include a positioning mount operative to set the first camera head in a given position and orientation to measure the first signals and to set the second camera head in the given position and orientation to measure the second signals.

Typically, the first volume includes a first conic volume, and the second volume includes a second conic volume concentric with the first conic volume.

The apparatus may include a positioning mount operative to set the first collimator channel in a first position and orientation with respect to the first detector element so as to measure the first signals and to set the second collimator channel in a second position, and orientation with respect to the second detector element so as to measure the second signals. Typically, the first collimator channel is fixedly coupled to the second collimator channel, and the first collimator channel and the second collimator channel are included in a common configurable collimator of the first and second camera heads.

In an embodiment, at least one of the first and second collimator channels has a plurality of dimensional configurations defining respective different sets of volume, elements of the body from which the radiation is emitted.

There is further provided, according to an embodiment of the present invention, a method for detecting radiation emitted from a number of volume elements of a body, including:

providing a first plurality of detector elements, each detector element being configured to output signals indicative of an intensity of radiation that is incident thereon;

positioning a first plurality of adjustable collimator channels between a respective detector element and the body, each adjustable collimator channel having a second plurality of dimensional configurations defining respective different sets of the volume elements from which emitted radiation impinges on the respective detector element; and computing a radiation intensity from at least a portion of the volume elements in response to the signals output by the detector elements in at least two of the dimensional configurations of the adjustable collimator channels.

There is further provided, according to an embodiment of the present invention, a; method for detecting radiation emitted from a body, including:

positioning a first collimator channel between, a first detector element and the body so as to define a first volume of the body from which emitted radiation impinges on the first detector element, the first detector element being operative to output first signals indicative of a first radiation intensity;

positioning a second collimator channel between a second detector element and the body so as to define a second volume of the body from which emitted radiation impinges on the second detector element, the second detector element being operative to output second signals indicative of a second radiation intensity, the second volume being smaller than and included in the first volume; and computing a radiation intensity from, at least a portion of the body in response to the first signals and the second signals.

There is further provided, according to an embodiment of the present invention, apparatus for detecting radiation emitted from a body, the apparatus including:

a detector element, which is operative to output signals indicative of an intensity of radiation that is incident thereon;

an adjustable collimator channel, positioned between the detector element and the body so as to define a volume of the body from which emitted radiation impinges on the detector element, and having at least a first configuration in which the emitted radiation impinges on the detector element from a first volume and a second configuration in which the emitted radiation-impinges on the detector element from a second volume smaller than and included in the first volume; and a processor coupled to compute a radiation intensity from at least a portion of the volume in response to the signals output by the detector element in at least the first and second configurations of the adjustable collimator channel.

There is further provided, according to an embodiment of the present invention, a method for detecting radiation emitted from a body, including:

outputting, from a detector element, signals indicative of an intensity of radiation that is incident on the detector element;

positioning an adjustable collimator channel between the detector element and the body so as to define a volume of the body from which emitted radiation impinges on the detector element, the adjustable collimator channel having at least a first configuration in which the emitted radiation impinges on the detector element from a first volume and a second configuration in which the emitted radiation impinges on the detector element from a second volume smaller than and included in the first volume; and computing a radiation intensity from at least a portion of the volume in response to the signals output by the detector element in at least the first and second configurations of the adjustable collimator channel.

The present invention will be more fully understood from the following detailed description of the embodiments thereof, taken together with the drawings in which:

BRIEF DESCRIPTION OF THE DRAWINGS

FIGS. 11A, 11B and 11C are schematic views of a disclosed collimator, according to an embodiment of the present invention;

FIG. 14 is a schematic diagram of an adjustable collimator channel formed in a cavity, according to an embodiment of the present invention.

DETAILED DESCRIPTION OF EMBODIMENTS

Figure 1:
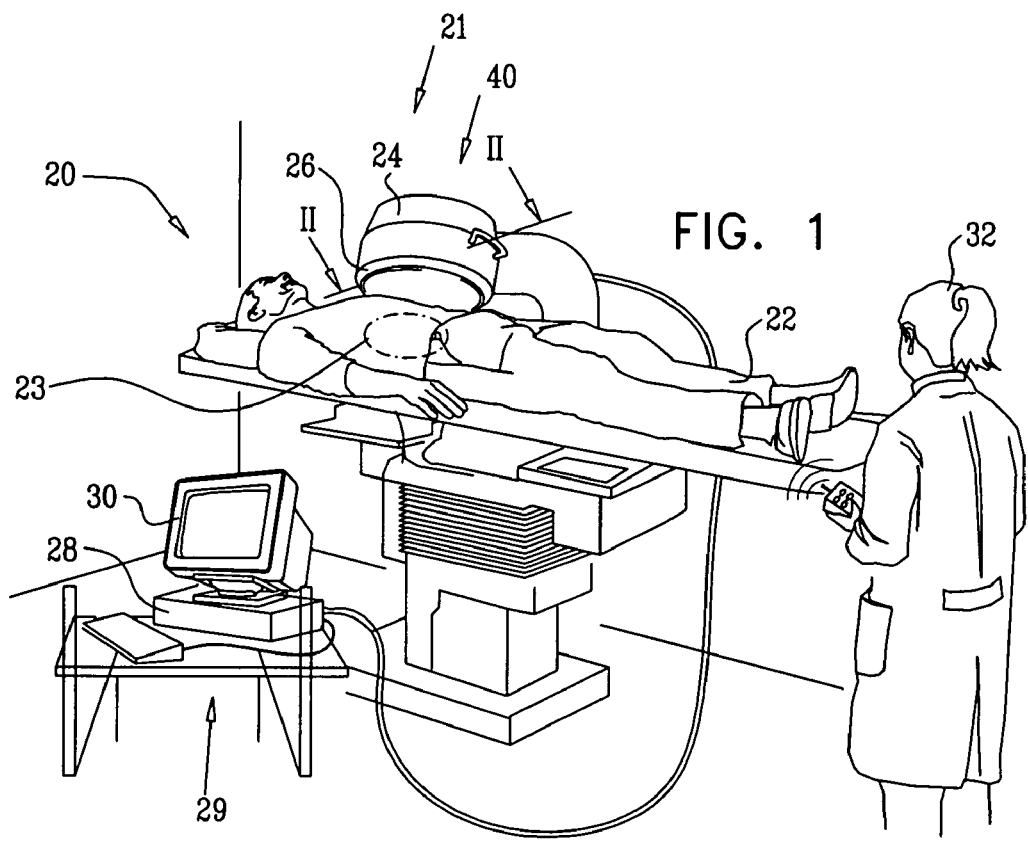
FIG. 1 is a schematic, pictorial illustration of a radiation detection system with an adjustable collimator, according to an embodiment of the present invention.

FIG. 1 is a schematic, pictorial illustration of a radiation detection system 20, according to an embodiment of the present invention. A radiopharmaceutical having a radioisotope tracer is administered to a patient's body 22. A radiation detecting device 21, typically an X-ray camera or a gamma-ray camera, senses radiation emitted from sites in a region 23 of body 22 that have absorbed the radioisotope tracer. Depending on the procedure being followed in using system 20, region 23 may comprise a part or all of body 22. Device 21 is hereinbelow, by way of example, assumed to comprise a gamma-ray camera head 24. Camera head 24 comprises a collimator 26 and detector elements 40, herein also referred to as detectors 40. Elements 40 typically comprise electrodes coupled to a semiconducting material such as Cadmium Zinc Telluride. Such detector elements are known in the art, and an example of a detector having such detector elements is described in U.S. Pat. No. 5,847,398 to Shahar, et al., which is incorporated herein by reference. Alternatively, detectors 40 may be formed from scintillators. Detectors 40 may be used for measuring X-rays and may operate by photon counting or current integration. Unless stated otherwise, in the description hereinbelow detectors 40 are assumed to comprise electrodes coupled to a semiconducting material. A cross-section of the collimator and the detectors is shown in more detail in FIG. 2.

Camera head 24 transmits to a processor 28 signals indicative of the radiation from region 23 reaching detectors 40. Processor 28 typically processes the signals to determine radioisotope absorption sites, as well as concentrations of the radioisotope at the sites. Processor 28 may also be coupled to a display 30 or to other image generating means, such as a printer, which may provide a map or image of the absorption sites and concentrations therein for analysis by an operator 32 of system 20. To perform its operations processor 28 uses a memory 29 to store the signals from the camera. Memory 29 also stores software for analysis of the signals, and results of the analysis, as is described in more detail below.

Figure 2:
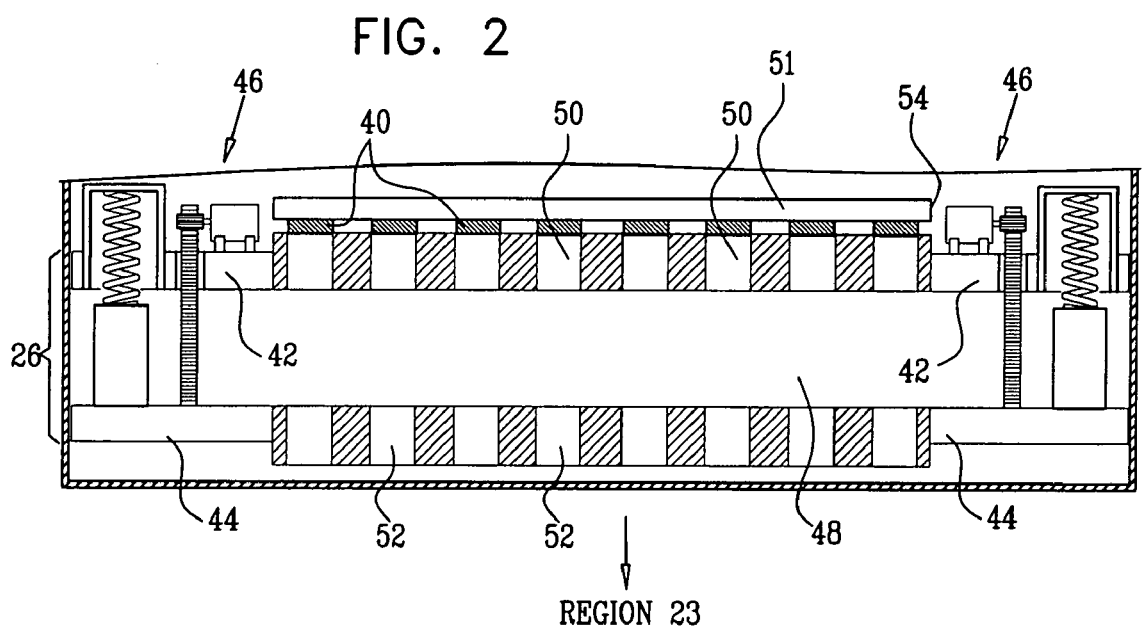
FIG. 2 is a schematic, cross-sectional view of the adjustable collimator of FIG. 1, according to an embodiment of the present invention.

FIG. 2 is a schematic view of a cross-section of camera head 24, in a plane perpendicular to a virtual line II (FIG. 1), according to an embodiment of the present invention. The cross-section shows collimator 26, which is positioned between the patient's body and detectors 40. Detectors 40 comprise a multiplicity, of similar electrodes mounted together, typically as a rectangular or hexagonal array, on a semiconducting material 51, which acts as a detector mounting 54.

Collimator 26 comprises two collimation plates, a collimation plate 42 adjacent the detector mounting, and a collimation plate 44, which faces region 23. Plate 42 is configured to cover detector elements 40, and plate 44 is generally similar in form to plate 42. Plates 42 and 44 are coupled to each other by a set of, brackets 46, which are adjustable so as to vary the width of a gap 48 between the plates. Alternatively or additionally, plates 42 and 44 may be coupled together by any other convenient adjustable coupling system known in the art, such as clamps and/or braces. Brackets 46 may set the width of gap 48 based on external automated control, such as control by processor 28, or, alternatively, by, manual control. Additionally, a sensor (not shown) may sense the gap width and transmit the value to processor 28 so that the processor may control the gap. Furthermore, the distance between mounting 54 and plate 42 may also be, varied, typically by a coupling system similar to that described above, and which for reasons of clarity is not shown in FIG. 2. It is to be understood that the horizontal orientation of the two plates and mounting 54 indicated in FIG. 2 is merely for the purpose of elucidation and that collimator 26 comprising the two joined plates may be oriented in any suitable direction vis-à-vis region 23. The distance of collimator 26 from region 23 may also be adjusted by processor 28.

Plates 42 and 44 are made of a material which is selected to be opaque to the radiation emitted by the radioisotope. Such materials typically comprise lead and/or tungsten, although other materials for forming collimator channels are known in the art. Holes through plate 42, indicated as collimator channels 50, are aligned with detector elements 40 and with holes in plate 44, indicated as collimator channels 52. Channels 50 and 52 typically have circular, rectangular, or hexagonal cross-sections, although embodiments of the present invention are not limited to a particular cross-sectional shape for the channels. In some embodiments the cross-section of the collimator channels has the same shape as detector elements 40. Alternatively, the channel cross-section and detector element shape may be different. Herein, plates 42 and 44, and their associated collimator channels, are assumed, by way of example, to be formed by drilling holes in a solid sheet. However, other methods for forming the plates and their channels will be apparent to those having ordinary skill in the art, such as by using "honeycombs" of the opaque material, and/or by casting the material. All such methods are assumed to be comprised within the scope of the present invention.

Hereinbelow, except where otherwise stated, detectors 40 are assumed to be circular, and channels 50 and 52 are assumed to have circular cross-sections so that they are cylindrical prisms. Those with ordinary skill in the art will be able to adapt the description herein for detectors that are not circular, and/or for collimator channels that have non-circular cross-sections, thus forming non-circular prisms.

Collimator channels 50 and 52 permit some of the emitted radiation from region 23 to pass through collimator 26 so as to impinge on detectors 40. Inter alia, the amount of radiation passing through collimator 26 may be varied by adjusting gap 48, and/or by varying the distance of detectors 40 from plate 42. Examples of such variations are described further hereinbelow with reference to FIGS. 3A, 3B, and 3C.

Figure 3A:
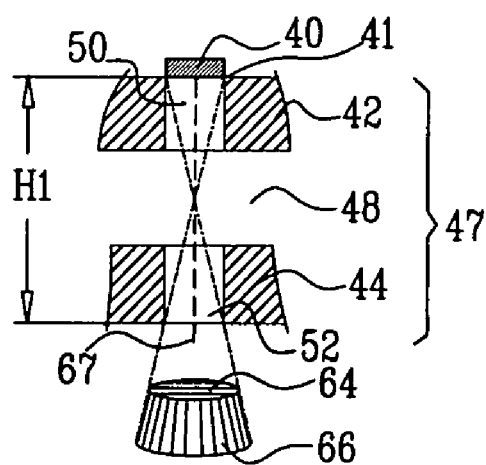
FIGS. 3A, 3B and 3C are schematic diagrams of dimensional configurations of a pair of collimator channels, according to an embodiment of the present invention.
Figure 3B:
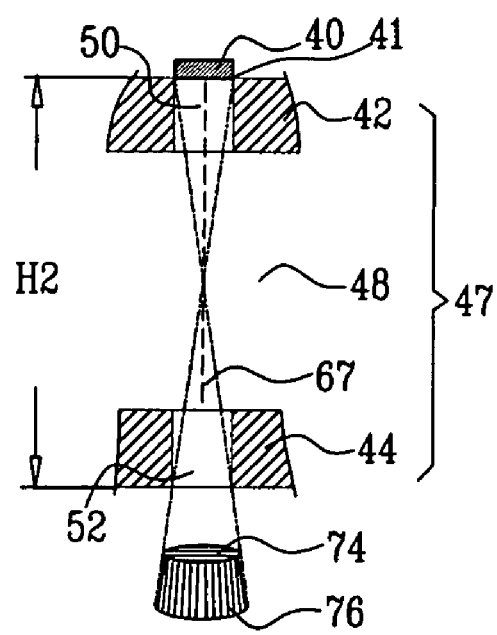
Figure 3C:
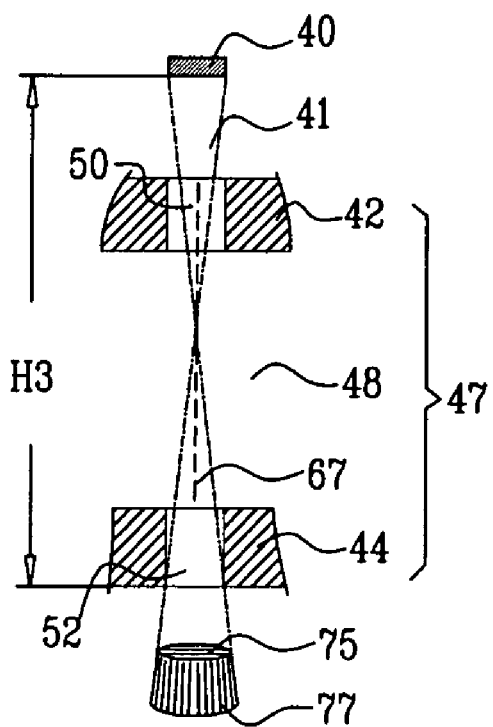

FIGS. 3A, 3B, and 3C are schematic diagrams of dimensional configurations of a pair 47 of collimator channels, according to an embodiment of the present invention. Pair 47 is also herein termed adjustable collimator channel 47. Adjustable collimator channel 47 is formed from a given collimator channel 50 and an associated collimator channel 52 within collimator 26 (FIG. 2). A respective detector 40 and adjustable collimator channel 47 define an axis of symmetry 67 of the adjustable collimator channel. In a first dimensional configuration of collimator 26, as illustrated in FIG. 3A, gap 48 between plates 42 and 44 is a relatively small distance H1, and a distance 41 between detector 40 and plate 42 is approximately 0. An effective length H1 of collimator 26, comprising the widths of plates 42 and 44 and the width of gap 48, is therefore relatively short. In this configuration, adjustable collimator channel 47 defines a volume 66 of region 23 (FIG. 1) from which emitted radiation may be received by the detector 40 associated with the channel. Radiation from this volume subtends a solid angle 64. Volume 66 is approximately in the shape of a frustum, although the base and the upper surface of the volume are bounded by the surface, of region 23 or of body 22, and are typically not parallel planes.

In a second dimensional configuration of collimator 26, illustrated in FIG. 3B, gap 48 between plates 42 and 44 is increased from that of the first configuration, and distance 41 remains at approximately 0. An effective length H2 of collimator 26 is longer than H1. In the second configuration, adjustable collimator channel 47 defines a volume 76 for received emitted radiation, volume 76 being smaller than, and included in, volume 66. Radiation from volume 76 subtends a solid angle 74, which is smaller than, and which is included in, solid angle 64.

In, a third dimensional configuration of, collimator 26, illustrated in FIG. 3C, gap 48 between plates 42 and 44 is the same as for the second configuration. Distance 41 has been changed so that it is greater than 0. An effective length H3 of collimator 26 is longer than H2. In the third configuration, adjustable collimator channel 47 defines a volume 77 for received emitted radiation, volume 77 being smaller than, and included in, volume 76. Radiation from volume 77 subtends a solid angle 75, which is smaller than, and which is included in, solid angle 74.

The configurations illustrated in FIGS. 3A, 3B, and 3C are implemented by changing dimensions of collimator channel 47, and/or by changing dimensions between the collimator channel and its associated detector 40. By varying these dimensions, a given collimator channel 47 may be arranged into a multiplicity of configurations, each configuration being selected to receive radiation from a different volume, such as are exemplified by volumes 66, 76, and 77. Embodiments of the present invention use a multiplicity of configurations of collimator 26 and detectors 40, as explained in more detail below, to determine concentrations of the radioisotope in different volume elements of region 23.

The description above exemplifies that volumes 77, 76, and 66 enclose each other. Other configurations of plates, 42 and 44, such as may be generated by plates 42 and 44 being translated horizontally with respect to each other, may generate a volume for each configuration that may not completely enclose each other. Such configurations will be apparent to those having ordinary skill in the art, and all such configurations are assumed to be comprised within the scope of the present invention.

Figure 4A:
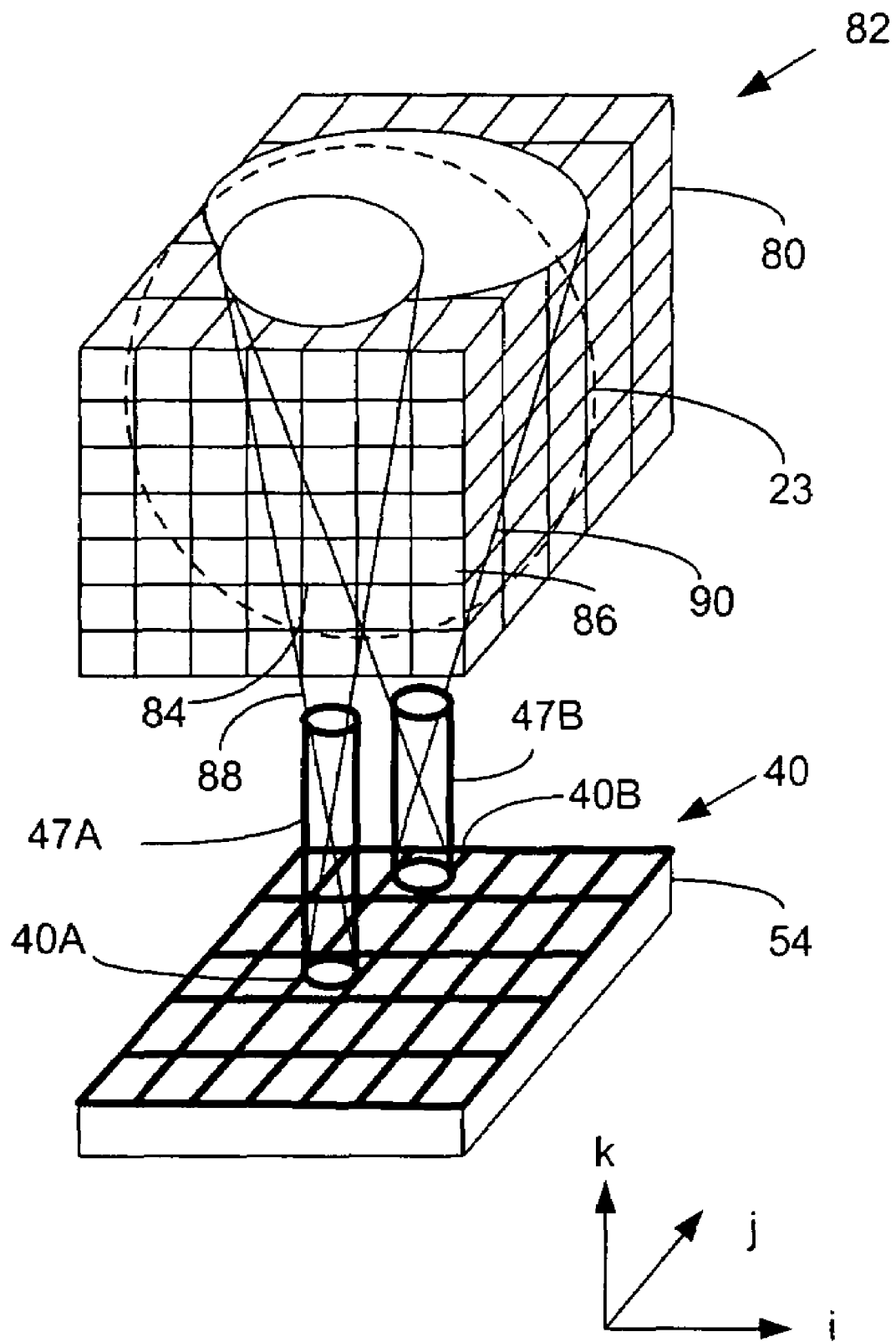
FIGS. 4A, 4B, and 4C are schematic diagrams illustrating a method of partitioning a region being investigated, according to an embodiment of the present invention.
Figure 4B:
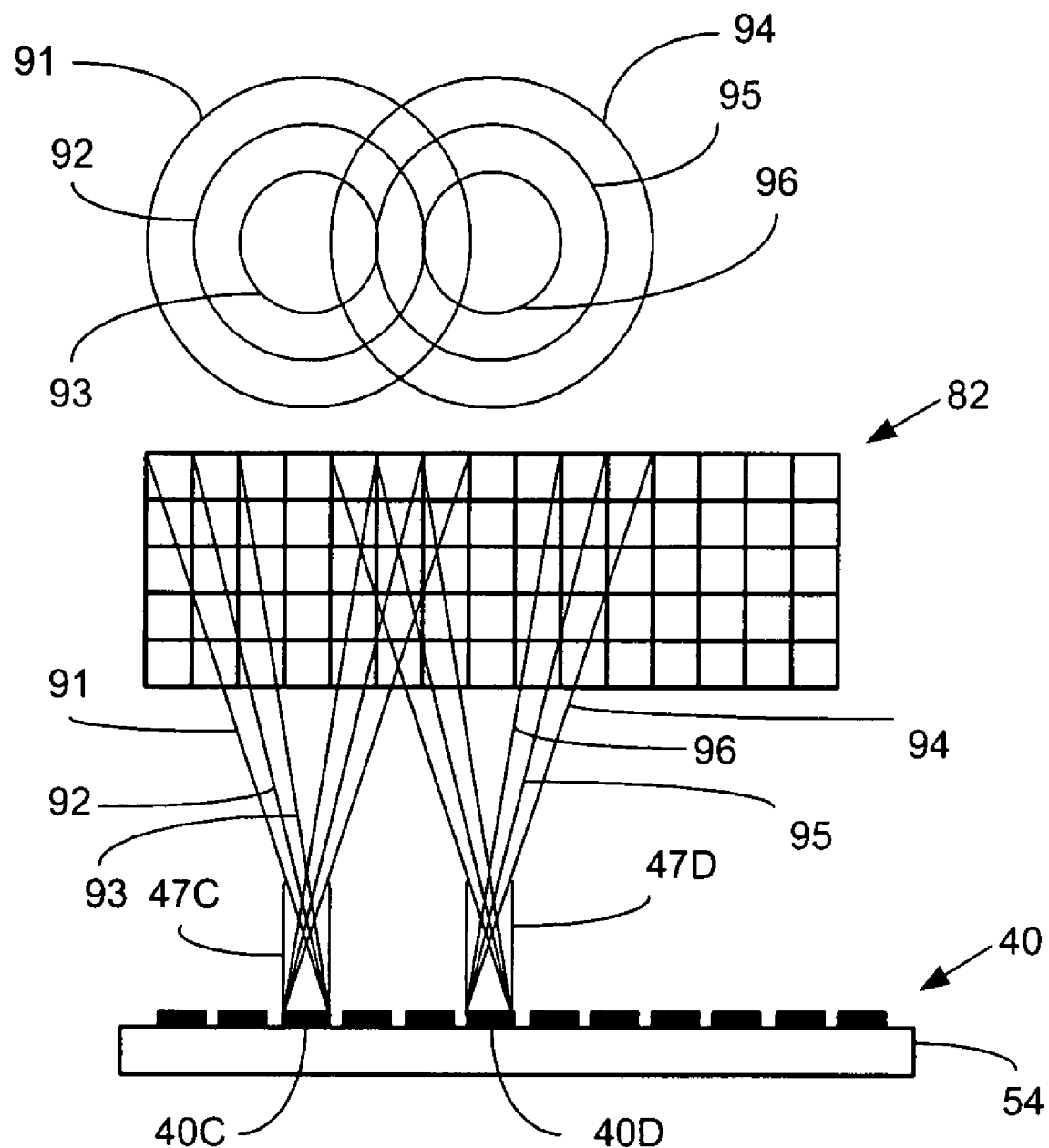
Figure 4C:
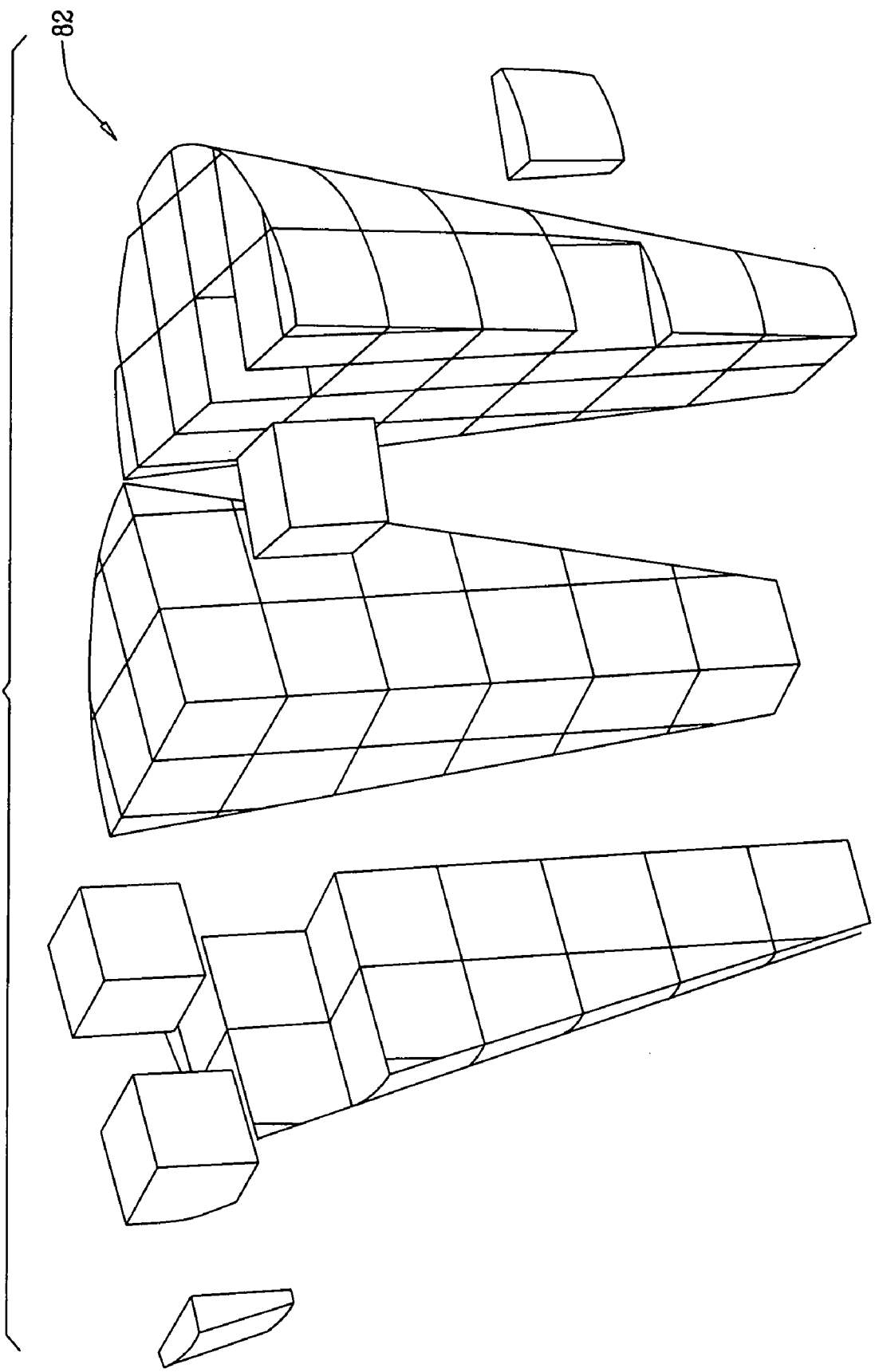

FIGS. 4A, 4B, and 4C are schematic diagrams illustrating a method of partitioning region 23 (FIG. 1), according to an embodiment of the present invention. In FIG. 4A region 23 is assumed to be enclosed in a volume 80, which is divided into a set of similarly shaped volume elements 82. Volume elements 82 are also herein termed voxels 82. Typically, voxels 82 are parallelepipeds, although voxels 82 may comprise any other shapes, such as triangular prisms, which can be arranged to completely fill the volume they enclose. Hereinbelow, except where otherwise stated, voxels 82 are assumed to comprise rectangular parallelepipeds, and volume 80 is also assumed to comprise a rectangular parallelepiped.

Detectors 40, mounted on detector mounting 54, are herein assumed to be rectangular in shape. Collimator channels 47 are assumed to be generally similar to those described with respect to FIGS. 3A, 3B, and 3C. In the following description, detectors 40 and collimator channels 47 are differentiated using letter suffixes, e.g., detectors 40A, 40B, . . . and collimator channels 47A, 47B, . . . .

For clarity only two collimator channels 47A and 47B are depicted in FIG. 4A, and the channels are shown as cylinders. Channels 47A and 47B are assumed to be respectively associated with detectors 40A and 40B. Although in operation of system 20 channels 47A and 47B typically have the same effective lengths, herein, for the purpose of explanation, channel 47A is assumed to have an effective length longer than that of channel 47B.

Detector 40A receives radiation from a set 84 of voxels and parts of voxels. The voxels and parts in set 84 are comprised of those elements that are included in a cone 88 defined by the dimensions of channel 47A, the dimensions of detector 40A, and the relative orientations and spacing between the collimator channel and the detector. Similarly, detector 40B receives radiation from a set 86 of voxels and parts of voxels. The elements in set 86 are comprised of those that are included in a cone 90 defined by the dimensions of channel 47B, the dimensions of detector 40B, and the relative orientations and spacing of the collimator channel and detector. Assuming that the only difference between the cone definitions is the difference in height of the two collimator channels, cone 86 encloses more voxels and parts of voxels than cone 88. As is apparent from the diagram, some voxels and parts of voxels are included in both cones.

FIG. 4B is a cross-section of voxels 82, detectors 40, and mounting 54, as shown in FIG. 4A. In FIG. 4B, cross-sections of cones 91, 92, 93, 94, 95, 96 generated by two collimator channels 47C and 47D, for respective detectors 40C and 40D, are shown. The collimator channels are shown in FIG. 4B as having their shortest effective height, and each channel, by way of example, has two other longer effective heights. Each collimator channel and detector combination thus generates three cones, so that detector 40C receives radiation from voxels and parts of voxels in cones 91, 92 and 93, and detector 40D receives radiation from elements in cones 94, 95, and 96. Bases of the cones are also shown in FIG. 4B.

FIG. 4C is a schematic exploded view of voxels 82 and parts of voxels included in a typical cone generated by a given detector 40 and associated collimator channel 47 not shown in FIG. 4C). FIG. 4C illustrates that complete voxels may be included in the cone, as well as parts of voxels that typically have differing shapes and volumes from each other.

As explained in more detail below, embodiments of the present invention use signals derived from different multiple sets of voxels and parts of voxels, such as, sets described in the examples above, to determine concentrations of radioisotopes in the voxels.

Figure 5:
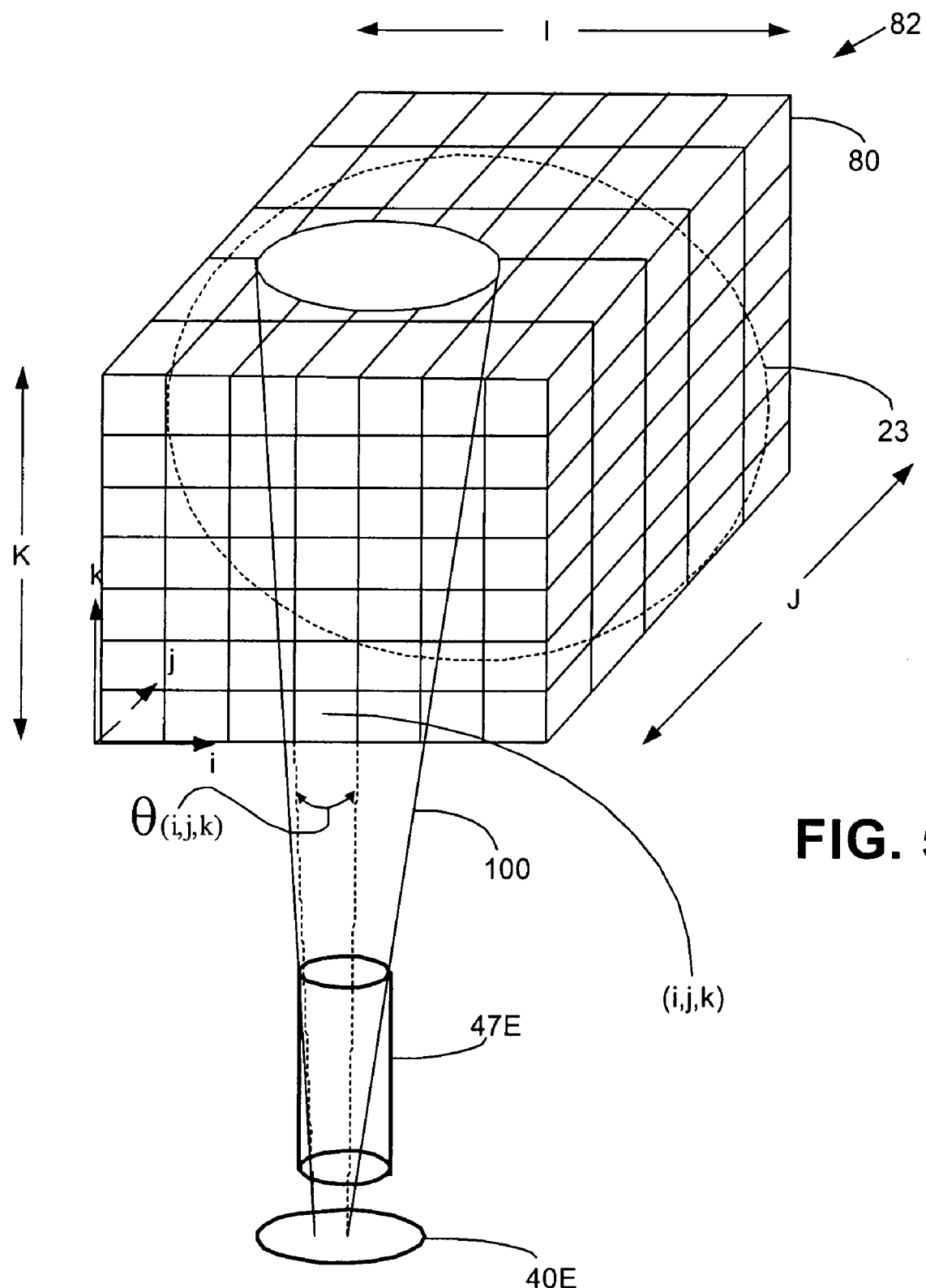
FIG. 5 is a schematic diagram illustrating a method for analysis of results obtained in operation of, the radiation detection system, according to an embodiment of the present invention.

FIG. 5 is a schematic diagram illustrating a method for analysis of results obtained in operation of system 20, according to an embodiment of the present invention. FIG. 5 shows an exemplary detector 40E and its associated collimator channel 47E, which have multiple different dimensional configurations, as have been described above. Detector 40E is also herein-referred to as detector d, d acting as an identifying index, or pixel number, of the detector. In a given one of the configurations, herein termed $conf_n$, detector d and collimator channel 47E define a generally conical or pyramidal structure 100, corresponding to a "viewing solid angle" for the detector. The actual dimensions and shape of structure 100 depend on the dimensions of detector d and collimator channel 47E, as well as on their relative positions, as is described above. In system 20 it is assumed that detector d and collimator channel 47E can be reconfigured to N different configurations, defining different structures generally similar to structure 100, referred to herein as $conf_1, \ldots, conf_n, \ldots, conf_N$, where N is a positive integer and n is any integer between 1 and N.

Region 23 is assumed to be enclosed in rectilinear volume 80, which is partitioned into a total of $M = I \cdot J \cdot K$ voxels 82, as described above (FIG. 4A). The M voxels are constructed on mutually orthogonal i, j, and k axes, and volume 80 has edges (in terms of numbers of voxels) I, J, and K. In the following description each voxel 82 may be uniquely identified by an ordered triple (i,j,k), where i, j, k are positive integers, or by a positive integer m, where $1 \leq m \leq M = I \cdot J \cdot K$.

During operation of system 20, there is an average concentration $C_{i,j,k}$ of radioisotope in each voxel (i,j,k), and the radiation intensity emitted by voxel (i,j,k) is linearly dependent on $C_{i,j,k}$. The intensity of radiation $I_{i,j,k}^{d,n}$ received by detector 40E from each voxel (i,j,k) is linearly dependent on a solid angle $\theta_{i,j,k}^{d,n}$ and a volume fraction $V_{i,j,k}^{d,n}$, both of which are subtended by the voxel (i,j,k) at detector 40E. When a channel such as channel 47E is associated with detector 40E and has configuration $conf_n$, then $V_{i,j,k} = 1$ if voxel (i,j,k) is completely enclosed by virtual structure 100 and $0 < V_{i,j,k} < 1$ if voxel (i,j,k) is partly enclosed by virtual structure 100.

The intensity $I_{i,j,k}$ emitted from a voxel (i,j,k) is given by:

$$I_{i,j,k} = C_{i,j,k} \cdot V_{i,j,k} \tag{1}$$

where $C_{i,j,k}$ is the average radioisotope concentration in voxel (i,j,k) and $V_{i,j,k}$ is the volume or partial volume of voxel (i,j,k).

Defining $I_{i,j,k}$ as the radiation intensity emitted from a complete voxel (i,j,k) when $V_{i,j,k} = 1$ and then $I_{i,j,k} = C_{i,j,k}$. According to this definition, when only a fraction $V_{i,j,k} < 1$ of voxel (i,j,k) is enclosed in virtual structure 100, then the radiation intensity emitted from such an incomplete voxel (i,j,k) is $I_{i,j,k} = C_{i,j,k} \cdot V_{i,j,k}$.

The intensity of radiation $I_{i,j,k}^{d,n}$ received by detector d from voxel (i,j,k) when the associated collimator is configured in $conf_n$, is given by:

$$I_{i,j,k}^{d,n} = \alpha_{i,j,k}^{d,n} \cdot C_{i,j,k} \theta_{i,j,k}^{d,n} \cdot V_{i,j,k}^{d,n} = \beta_{i,j,k}^{d,n} \cdot I_{i,j,k} \tag{2}$$

where $\alpha_{i,j,k}^{d,n}$ is a linearizing constant of voxel (i,j,k) also known as the absorption/attenuation factor between voxel (i,j,k) and detector d associated with a collimator in configuration $conf_n$.

In a situation without absorption and scattering $\alpha_{i,j,k}^{d,n}$ is equal to 1. Expression (2) may also be written in the form:

$$I_{i,j,k}^{d,n} = \beta_{i,j,k}^{d,n} \cdot I_{i,j,k} \tag{2a}$$

where $\beta_{i,j,k}^{d,n} = \alpha_{i,j,k}^{d,n} \cdot \theta_{i,j,k}^{d,n} \cdot V_{i,j,k}^{d,n}$ is the proportional coefficient between the radiation intensity $I_{i,j,k}^{d,n}$ received by a detector d from voxel (i,j,k) and the radiation $I_{i,j,k}$ emitted from voxel (i,j,k) when the associated collimator is configured in $conf_n$.

From expressions (2) and (2a), the total intensity $S^{d,n}$ received by detector d from all the voxels (i,j,k) defined by virtual structure 100 corresponding to configuration $conf_n$ of the collimator is given by:

$$S^{d,n} = \sum_{i,j,k}^{conf_n} I^{d,n} \tag{3}$$

$$= \sum_{i,j,k}^{conf_n} \alpha_{i,j,k}^{d,n} \cdot C_{i,j,k} \cdot \theta_{i,j,k}^{d,n} \cdot V_{i,j,k}^{d,n}$$

$$= \sum_{i,j,k}^{conf_n} \beta_{i,j,k}^{d,n} \cdot I_{i,j,k}$$

where the sum in expression (3) is taken over all voxels (i,j,k) wholly or partly included in configuration $conf_n$, $\alpha_{i,j,k}^{d,n}$ is the attenuation factor between voxel (i,j,k), and detector d associated with collimator channel in configuration $conf_n$, $\theta_{i,j,k}{}^{d,n}$ is the solid angle in which voxel (i,j,k) is viewed from detector d associated with collimator channel in configuration conf$_n$, $V_{i,j,k}{}^{d,n}$ is the volume fraction of voxel (i,j,k) enclosed by structure 100 as viewed from detector d associated with a collimator channel in configuration conf$_n$, and $\beta_{i,j,k}{}^{d,n} = \alpha_{i,j,k}{}^{d,n} \cdot \theta_{i,j,k}{}^{d,n} \cdot V_{i,j,k}{}^{d,n}$ is the proportional coefficient between the intensities of the radiation emitted from voxel (i,j,k) and the radiation received from voxel (i,j,k) at detector d associated with collimator channel in configuration conf$_n$.

In expression (3) the values of i,j, and k are chosen to correspond to the same voxel. Similarly, the values of d and n are chosen to correspond to the same detector and collimator configuration, respectively.

Expression (3) may also be written in the form $$S^{d,n} = \beta_{1,1,1}{}^{d,n} \cdot I_{1,1,1} + \ldots + \beta_{I,J,K}{}^{d,n} \cdot I_{i,j,k} \quad (4)$$

where I,J,K are the maximum values of integers i,j,k.

It will be understood that for any specific value of i,j,k, a number of values of $\beta_{i,j,k}{}^{d,n}$ are 0, corresponding to those voxels and parts of voxels which are not included in the structure equivalent to virtual structure 100. Also, the products $\theta_{i,j,k}{}^{d,n} \cdot V_{i,j,k}{}^{d,n}$ are functions of the geometry of the detector configurations, and of the locations and dimensions of voxels (i,j,k). Thus, the values of $\theta_{i,j,k}{}^{d,n}$ may be pre-calculated from the detector configurations and voxel parameters. Similarly, the attenuation coefficients $\alpha_{i,j,k}{}^{d,n}$ may be found by attenuation mapping, also known as an attenuation correction method, which is known in the X-ray imaging art. Alternatively, $\alpha_{i,j,k}{}^{d,n}$ may be assumed to be equal to 1. Accordingly, the proportional coefficients $\beta_{i,j,k}{}^{d,n} = \alpha_{i,j,k}{}^{d,n} \cdot \theta_{i,j,k}{}^{d,n} \cdot V_{i,j,k}{}^{d,n}$ may be pre-calculated from the detector configurations and voxel parameters as well.

Herein it is assumed that there are D detectors (pixels) in camera head 24, each detector and its associated collimator channel having N configurations. Accordingly, D and N are the maximum values for integers d,n, respectively.

Thus, in total, there are D·N expressions similar to expression (4):

$$S^{1,1} = \beta_{1,1,1}^{1,1} \cdot I_{1,1,1} + \ldots + \beta_{I,J,K}^{1,1} \cdot I_{I,J,K}$$
$$\vdots$$
$$\cdot S^{D,N} = \beta_{1,1,1}^{D,N} \cdot I_{1,1,1} + \ldots + \beta_{I,J,K}^{D,N} \cdot I_{I,J,K} \quad (5)$$

Expressions (5) are D·N simultaneous linear equations where the coefficients $\beta_{i,j,k}{}^{d,n} = \alpha_{i,j,k}{}^{d,n} \cdot \theta_{i,j,k}{}^{d,n} \cdot V_{i,j,k}{}^{d,n}$ are known and their values may be pre-calculated. The values of $\beta_{i,j,k}{}^{d,n}$ may be calculated from the geometrical relations between the positions of the measured object, the detector and the configuration of the collimator. For example, as illustrated by FIGS. 3A-3C, the coefficients of $\beta_{i,j,k}{}^{d,n}$ can be calculated from the size of detector 40, the distance H1, gap 48 between channels 42 and 44, the distance of detector 40 from channel 42 and the distance between volume 66 and channel 44. The values of these geometrical parameters may be provided by an operator into processor 28 which in turn calculates coefficients $\beta_{i,j,k}{}^{d,n}$. Alternatively, the imaging system may include position sensors (not shown in FIGS. 3A-3C) to measure these geometrical parameters, so that they may be provided to processor 28 to calculate coefficients $\beta_{i,j,k}{}^{d,n}$.

There are M=I·J·K unknown intensities $I_{i,j,k}$ emitted from voxels i,j,k.

Accordingly, if $$D \cdot N = M = I \cdot J \cdot K \quad (6)$$

i.e., if the number M of voxels i,j,k is equal to the product of the number D of detectors and the number N of configurations of the detectors, then, as is known in the mathematical art, expressions (5) may be uniquely solved for all the intensities $I_{i,j,k}$ emitted from voxels i,j,k. The existence of a solution depends on the values of coefficients $\beta_{i,j,k}{}^{d,n}$. Methods for evaluating whether expressions (5) are solvable are well known in the art, and are explained, for example, in "A First Course in Numerical Analysis" by Ralston et al., published by McGraw-Hill.

In an, embodiment of the present inventions processor 28 sets the D detectors 40 and their associated collimator channels 47, of camera head 24, to have N configurations. For each configuration, the processor receives a signal from each detector, so that in total processor 28 receives D·N signals, corresponding to the values $S^{1,1} \ldots S^{D,N}$ of expressions (5). As is described below with reference to FIG. 6, processor 28 uses the signals received from the position sensors, indicating the value of the geometrical parameters mentioned above, to set a number of voxels within a region being imaged, and to find the radiation intensity $I_{i,j,k}$ or number of photons emitted by the radioisotope within each voxel.

The method of image-reconstruction described above has the following advantages:

High resolution.
High sensitivity.
Cross-section presentations.

As explained above, the size of voxels i,j,k, may be chosen as desired. Thus the size of these voxels may even be chosen to be smaller than the size of the detector (pixel) to achieve sub pixel resolution. The smaller the size of voxels i,j,k, the larger is their number M and thus the number of the linear equation in expression (5) should be larger and equal to M (D·N=I·J·K). This means that for increasing the resolution, the number of configurations N of the collimator associated with the detector should be increased as well to fulfill the requirement of expression (6).

In embodiments of the present invention the sensitivity of the camera head is increased-significantly in comparison with a camera head having a prior art collimator. The configurable collimator according to embodiments of the present invention has multiple configurations corresponding to multiple solid angles, of a collimator channel associated with a detector, through which the measured object is viewed and measured. Most of these angles are much larger than the solid angle of (a prior art collimator channel associated with a detector, through which the measured object is viewed and measured.

This results in better collection efficiency of the radiation emitted from the measured object and collected by the detectors and leads to a higher sensitivity in the embodiments according to the present invention.

The method described above is highly flexible for image display and presentation. Solving the system of equations written in expression (5) gives the values of the radiation intensity $I_{i,j,k}$, or number of photons, emitted by the radioisotope within each voxel i,j,k. Thus, as described below in relation to FIG. 7, the imaged volume of the object may be displayed by any desired cross-section or slice of the imaged object.

Figure 6:
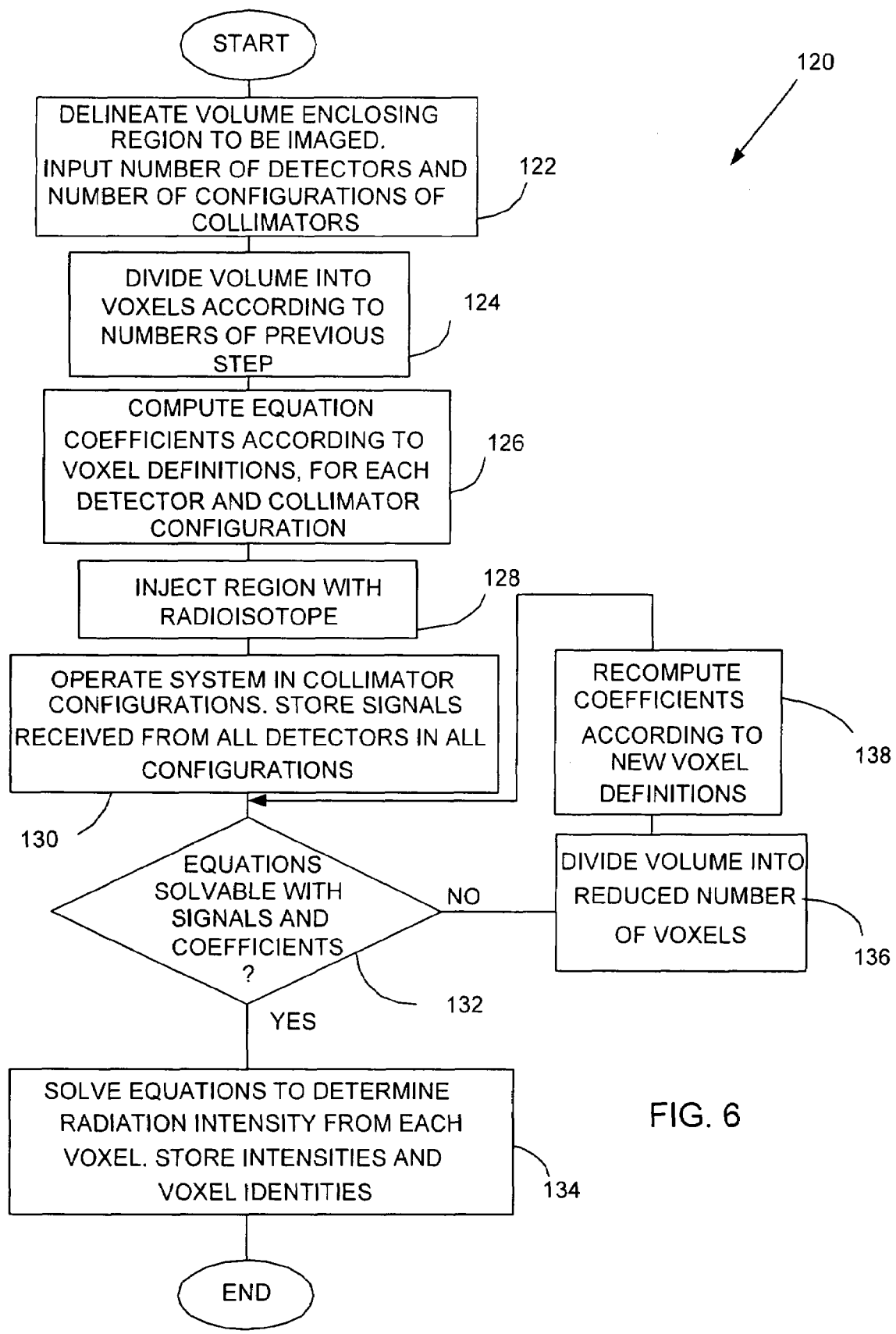
FIG. 6 is a flowchart showing steps performed by, a processor in operating a camera in the radiation detection system, according to an embodiment of the present invention.

FIG. 6 is a flowchart 120 showing steps performed by processor 28 in operating camera head 24, according to an embodiment of the present invention. In a first step 122, operator 32 delineates volume 80 (FIG. 5) enclosing region 23, and inputs the dimensions and location of the volume to processor 28. The operator also provides processor 28 with the number of detectors D, and the number of configurations N, that may be assumed by each detector.

In a second step 124, processor 28, under the supervision of the operator, divides volume 80 into M similarly shaped voxels, where the value of M is set, to be equal to or less than the product D·N. The actual value of M depends on the numbers of voxels in each edge of volume 80. Typically, the value of M is set to be as large as possible, given the constraints above. Voxels 82 may be cubes, or alternatively, the lengths of edges of voxels 82 may be set to be unequal.

In a third step 126, processor 28 computes the values of coefficients $\beta_{i,j,k}^{d,n}$, given the parameters determined in the first and second steps. The values are computed for all D·N combinations of d and n, and processor 28 stores the computed values.

In a fourth step 128, operator 32 injects the patient so that region 23 absorbs the radioisotope.

In a fifth step 130, system 20 is operated in its N configurations. In each of the configurations processor 28 receives and stores in memory 29 signals from each of the D detectors, so that for the N configurations the processor stores D·N signal values corresponding to $S^{1,1} \ldots S^{d,n}$.

In a sixth step 132, given the values of $\beta_{i,j,k}^{d,n}$ previously stored in step 126, and the signal values corresponding to $S^{1,1} \ldots S^{d,n}$ found in step 130, processor 28 determines if expressions (5) are solvable.

If, in step 132, processor 28 determines that expressions (5) are not solvable, in a step 136 the number of voxels into which volume 80 is divided is reduced, by increasing the dimensions of the voxels. The change in voxel dimension, and the corresponding reduction of number of voxels in volume 80, is performed by processor 28, typically under supervision of operator 32'. In one embodiment of the present invention, the number of voxels is reduced by decrementing by 1 the value of edge I, J, or K.

In a step 138, processor 28 recomputes the values of coefficients $\beta_{i,j,k}^{d,n}$ for all D·N combinations of d and n, and processor 28 stores the recomputed values. Flowchart 120 then returns to step 132.

If, in step 132, processor 28 determines that expressions (5) are solvable, the processor, in an intensity evaluation step 134, computes the intensities $I_{i,j,k}$, by solving the expressions, and stores the values of the intensities in association with identities (i,j,k) of respective voxels. Flowchart 120 then ends.

Consideration of flowchart 120 shows that processor 28 applies an iterative process to the D·N results it receives from camera head 24, and that the process generates a largest number of voxels into which region 23 may be divided. Forming the largest number of voxels corresponds to generating images of region 23, described in more detail with respect to FIG. 7, with a highest resolution.

Figure 7:
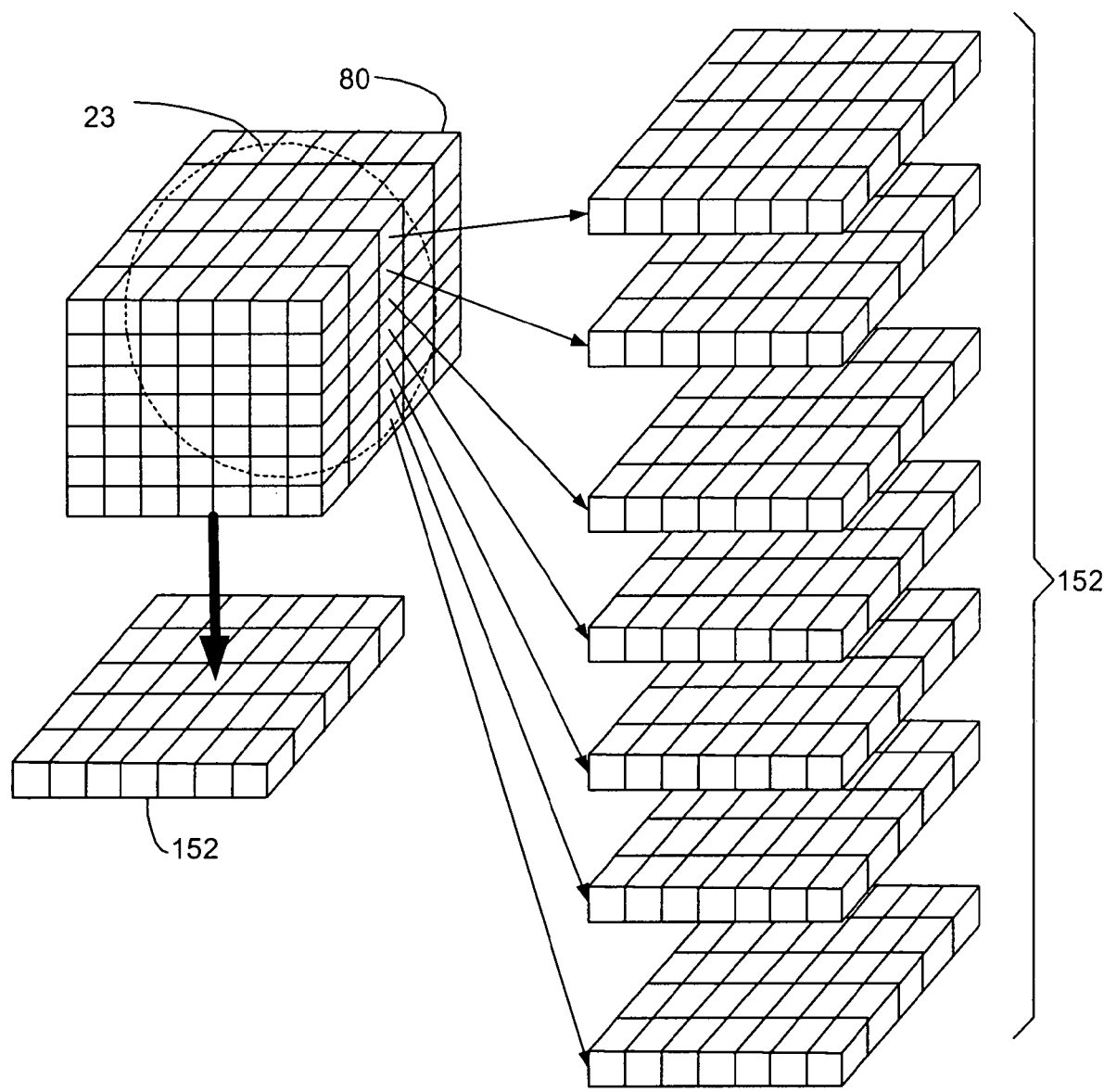
FIG. 7 illustrates sections of the region being investigated, that may be generated from the concentrations derived from the flowchart of FIG. 6, according to an embodiment of the present invention.

FIG. 7 illustrates sections of region 23 that may be generated from the intensities derived from flowchart 120, according to an embodiment of the present invention. Consideration of flowchart 120 shows that on completion of the flowchart, processor 28 has calculated the intensities $I_{i,j,k}$, of every voxel (i,j,k) in volume 80. Operator 32 uses processor 28 to display the resulting intensities on display 30, typically by selecting the complete set of voxels and displaying them in a perspective view, or alternatively by selecting subsets of the voxels, such as one or more slices 152 of voxels. Slices 152 may comprise planes normal to one of axes i, j, or k. Alternatively slices 152 may comprise planes which are non-normal to the axes. Further alternatively, processor 28 may select and display subsets of voxels that are comprised in one or more non-planar surfaces, such as sets of voxels of one or more surfaces similar to sections of an onion. In an alternative image presentation, the intensities of the voxels (i,j,k) may be added to form an image projection. For example all the intensities of voxels (i,j,k) may be summed along the columns of volume 80 to produced a two dimensional image projection similar to the image display received by a conventional collimator.

Those having ordinary skill in the art will appreciate that methods other than that exemplified by flowchart 120 may be used to determine, values of intensities $I_{i,j,k}$ from signals generated by detectors 40. For example, since for each of the N configurations a different volume of region 23 is subtended at each given detector 40, processor 28 may be configured to determine one or more differential signals, corresponding to respective one or more differential volumes of region 23. The differential volumes are typically in the form of annular volumes, such as are generated by taking a difference between volume 66 and volume 76 (FIGS. 3A and 3B). Processor 28 may be arranged to compute intensities $I_{i,j,k}$ from the overlap of differential volumes generated by different detectors 40. Other methods for generating, the intensities will be familiar to those having ordinary skill in the art, and all such methods are included in the scope of the present invention.

FIGS. 8A-14 described below illustrate alternative collimators to collimator 26, according to embodiments of the present invention. Each alternative collimator performs generally the same function as collimator 26, enabling each detector 40 in camera head 24 to receive radiation from different volumes of region 23. As appropriate, mounting 54 and/or detectors 40 are shown in each illustration of the alternative configurations.

Figure 8A:
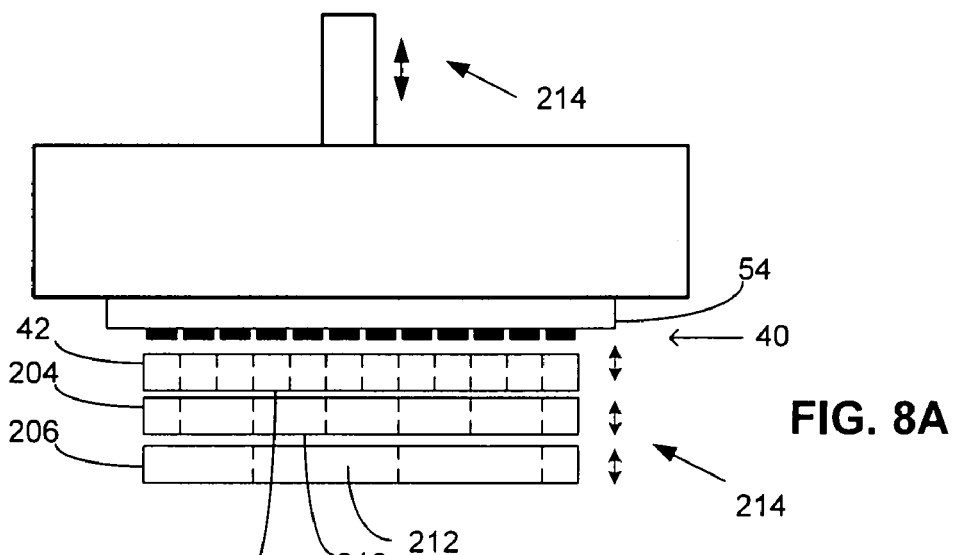
FIGS. 8A and 8B are schematic cross-sectional views of one collimator.
Figure 8B:
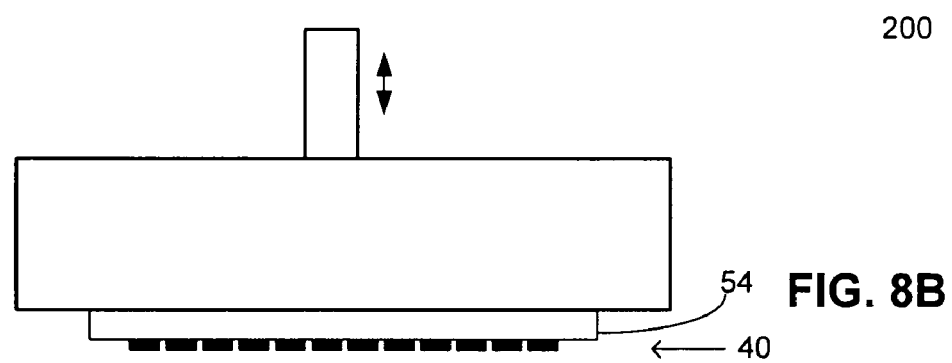
Figure 8C:
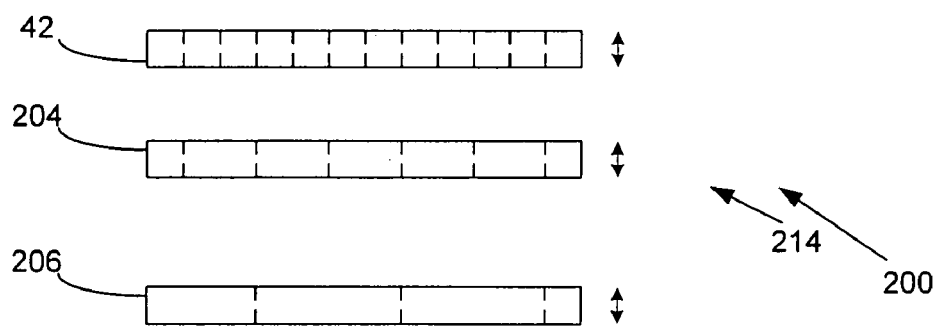
FIG. 8C is a view of detectors and collimator channels of the collimator, according to an embodiment of the present invention.
Figure 8C:
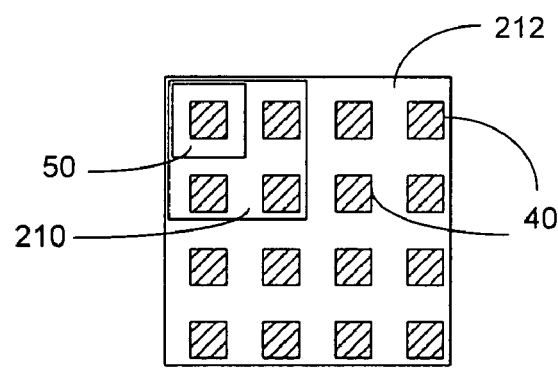

FIGS. 8A and 8B are schematic cross-sectional views of a collimator 200, and FIG. 8C is a view of, detectors and collimator channels of the collimator, according to an embodiment of the present invention. Apart from the differences described below, the operation of collimator 200 is generally similar to that of collimator 26 (FIG. 2), such that elements indicated by the same reference numerals in both collimators 26 and 200 are generally identical in construction and in operation. Collimator 200, comprises three plates 42, 204, and 206, which processor 28 may move vertically with respect to each other. Processor 28 may also move detectors 40 on mounting 54 vertically with respect to the plates. As described above with reference to FIG. 2, plate 42 comprises collimator channels 50, each of which is aligned with a respective detector 40. In collimator 200, by, way of example detectors 40 are assumed to have rectangular cross-sections. Also, detectors 40 are assumed to be distributed in a two-dimensional rectangular array defined by two orthogonal repetition vectors. Each collimator channel 50 is also assumed to have a rectangular cross-section, which encloses a vertical projection of its associated detector 40. Collimator channels 50 are distributed in a two-dimensional rectangular array having substantially the same repetition vectors as those which define the two-dimensional array in which detectors 40 are distributed. FIG. 8C shows a view of detectors 40 and one collimator channel 50.

Plate 204 is generally similar to plate 42, but has collimator channels 210 instead of channels 50. Each collimator channel 210 has a rectangular cross-section, so, that each channel aligns with four detectors 40 arranged as a 2×2 pattern. Collimator channels 210 are distributed in a two-dimensional rectangular array defined by two orthogonal repetition vectors which are double the repetition vectors defining the two-dimensional array in which detectors 40 are distributed.

Plate 206 is also generally similar to plate 42, but has collimator channels 212 instead of channels 50. Each collimator channel 212 has a rectangular cross-section, so that each channel aligns with 16 detectors 40 arranged as a 4×4 pattern. Collimator channels 212 are distributed in a two-dimensional rectangular array defined by two orthogonal repetition vectors which are four times the repetition vectors defining the two-dimensional array of detectors 40. FIG. 8C illustrates the relation between detectors 40, and collimator channels 50, 210 and 212.

By positioning plates 42, 204, and 206 differently with respect to detectors 40, as illustrated by arrows 214, processor 28 may set different configurations for the detectors of collimator 200. Each set of positions for the plates and detectors corresponds to a different configuration for collimator 200. For each different configuration, each detector 40 receives radiation from a set of voxels or parts of voxels in region 23, the sets typically being different for each different configuration. Each of the sets is defined by a generally pyramidal shape which encloses region 23, the pyramidal shape being set by the positions of plates 42, 204, and 206, and the position of detectors 40. Unlike the generally conical shapes defined by the collimator plates of collimator 26, the generally pyramidal shapes generated by collimator 200 typically do not have common axes of symmetry. Typically, for a given detector 40, the sets of voxels or parts of voxels defined by the different configurations at least partly include each other.

Figure 9A:
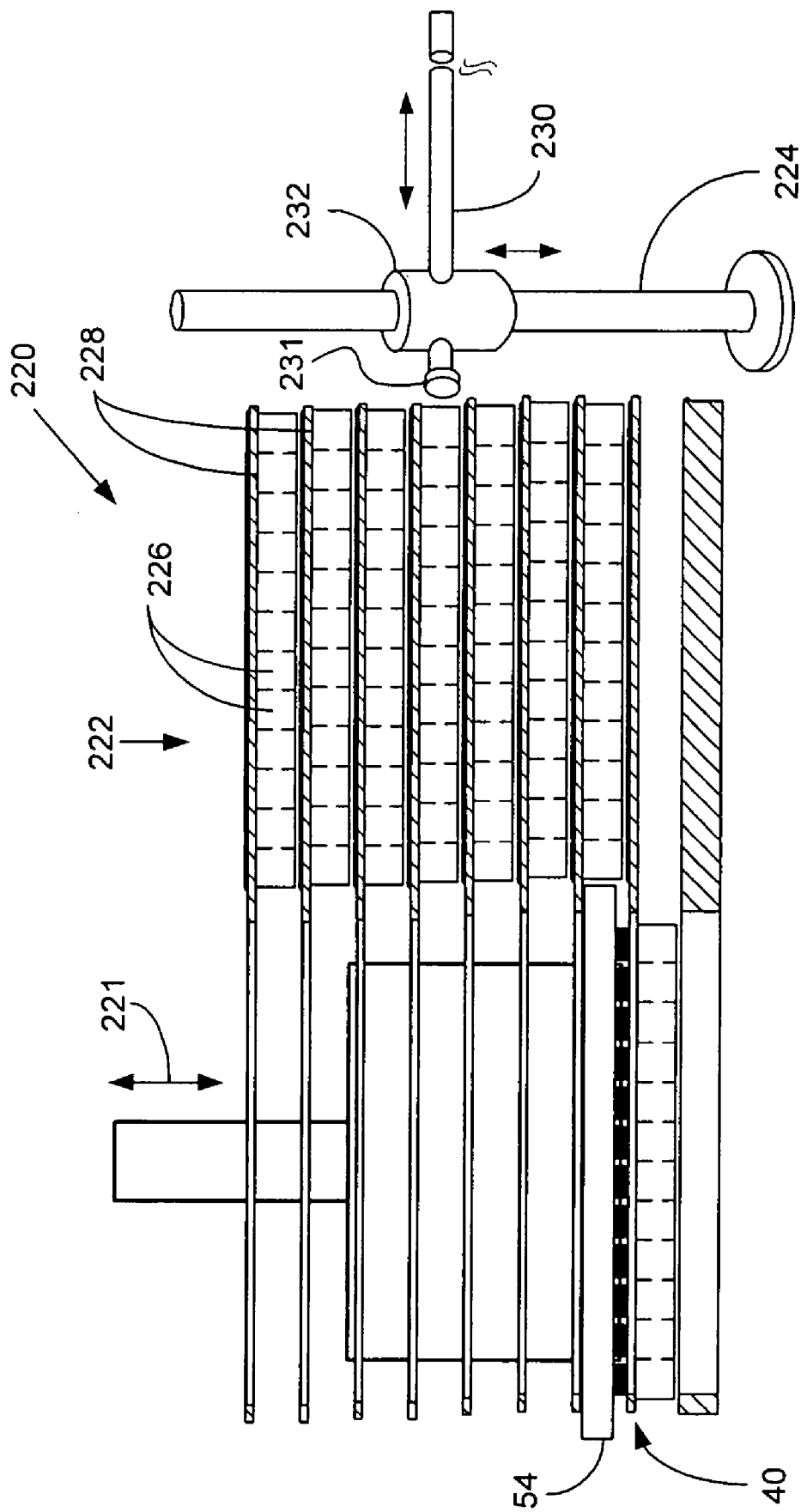
FIGS. 9A and 9B are schematic views of an alternative collimator, according to an embodiment of the present invention.
Figure 9B:
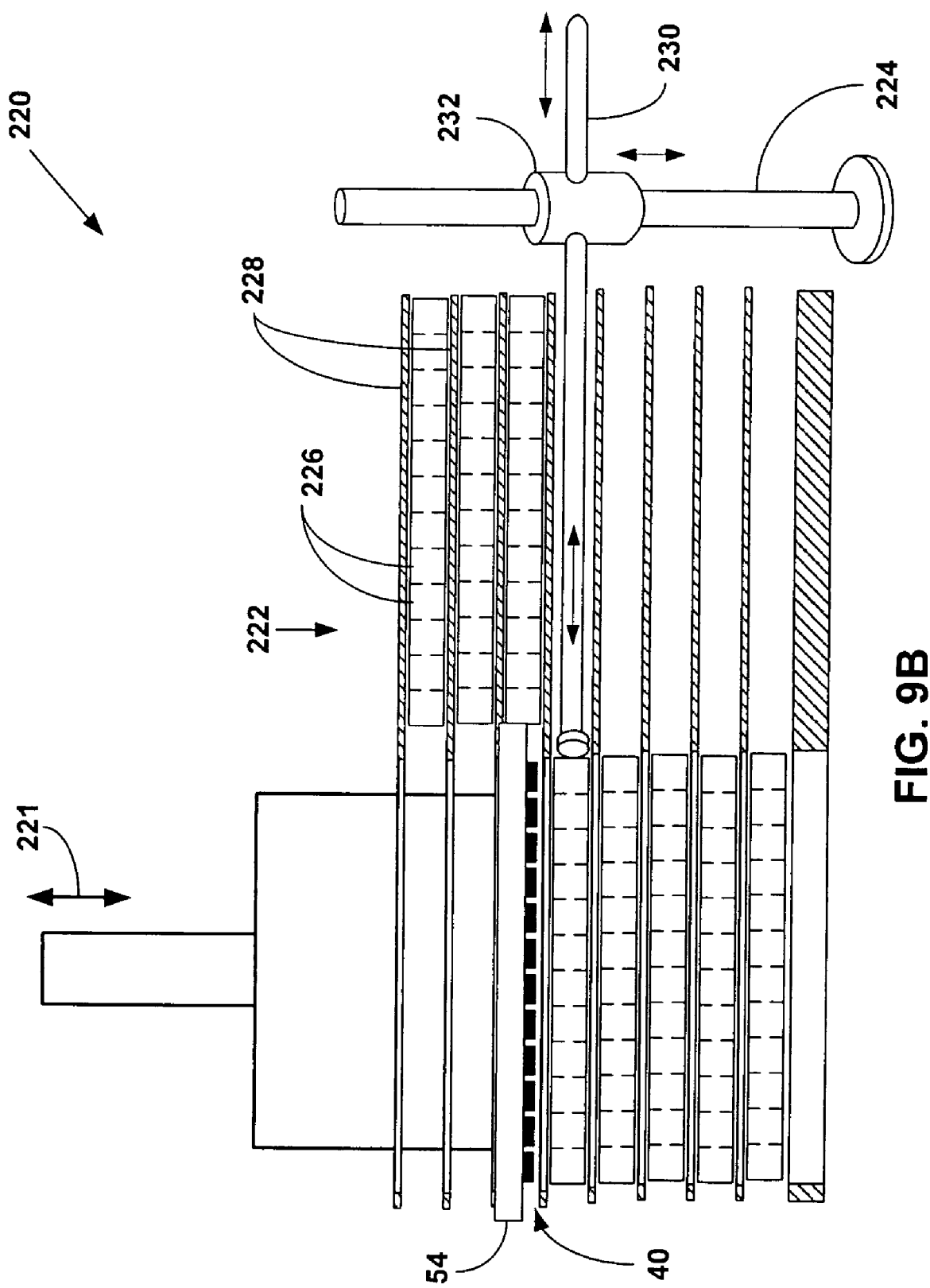

FIGS. 9A and 9B are schematic views of a collimator 220, according to an embodiment of the present invention. Collimator 220 comprises a plurality of generally similar plates 222. Plates 222 are generally similar to plate 42 (FIG. 2), each plate 222 having collimator channels 226, which are generally similar to channels 50. Collimator channels 226 may be aligned with detectors 40, by processor 28 moving each plate 222 into alignment with detectors 40, or the processor may move each plate so that its collimator channels are completely out of alignment. Processor 28 moves the plates into and out of alignment by sliding the plates horizontally on tracks 228, using a plate alignment mechanism 224. Alignment mechanism 224 comprises a rod 230, which is configured to push the plates horizontally into alignment, or to pull them out of alignment. In one embodiment, plates 222 are pushed/pulled into/out of alignment by rod 230 having a magnet edge 231 that allows rod 230 to pull plates 222 out of alignment by magnetizing the ferromagnetic frame of plates 222 with rod 230. Mechanism 224 also comprises a vertical translator 232, which is able to position rod 230 against any of plates 222. Processor 28, operates mechanism 224. Typically, processor 28 may also move detectors 40 vertically with respect to plates 222, as indicated by double-headed arrow 221, so as to maintain the distance from the detectors to an uppermost plate 222 approximately constant.

By way of example, FIG. 9A shows one lower plate 222 in alignment with the detectors, and seven upper plates moved out of alignment. FIG. 9B shows five lower plates 222 in alignment with the detectors, and three upper plates moved out of alignment. It will be apparent that collimator 220 may be configured into seven configurations, each configuration allowing each given detector 40 to receive radiation from seven different volumes of region 23.

Figure 10A:
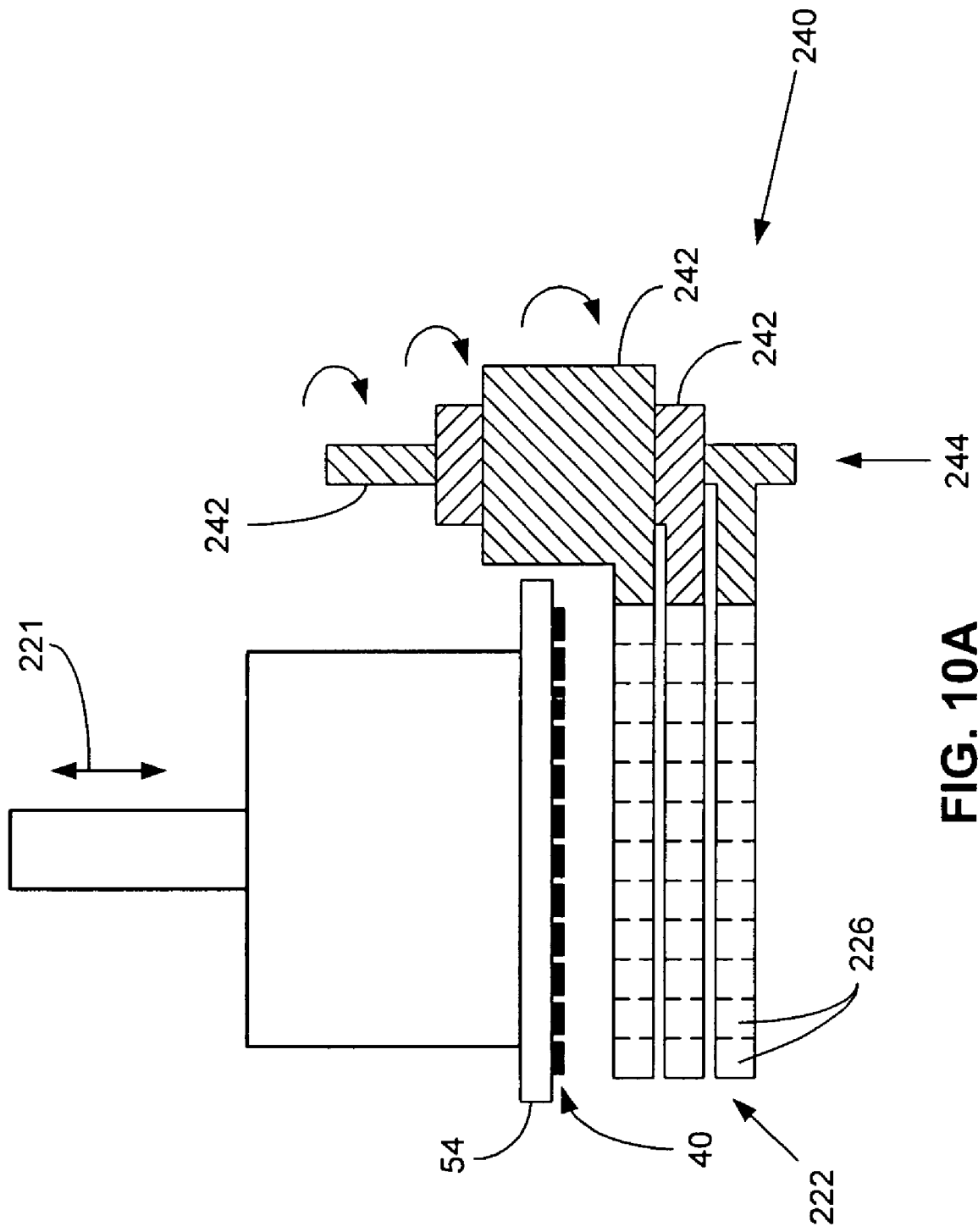
FIGS. 10A and 10B are schematic views of a further alternative collimator, according to an embodiment of the present invention.
Figure 10B:
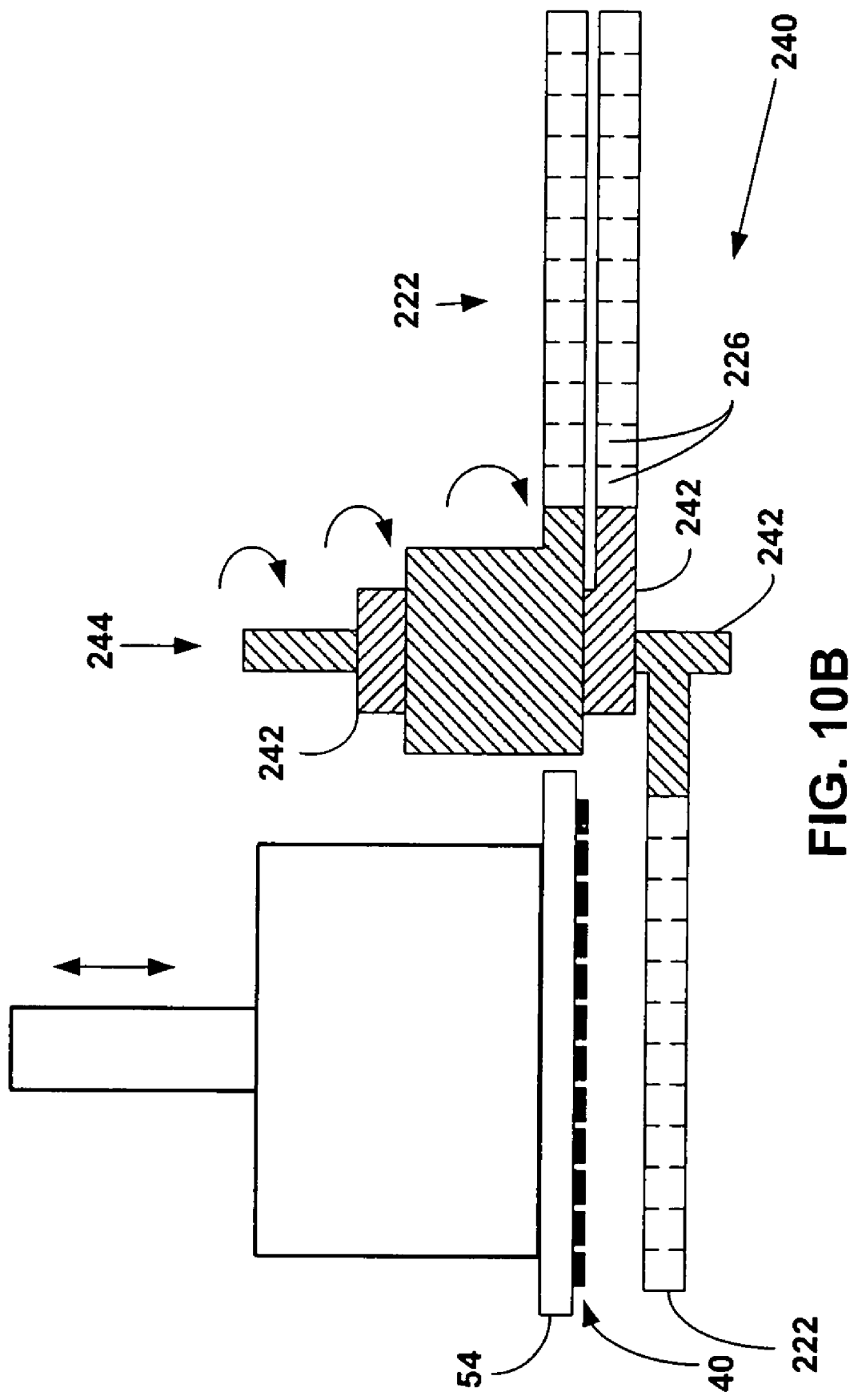

FIGS. 10A and 10B are schematic views of a collimator 240, according to an embodiment of the present invention. Apart from the differences described below, the operation of collimator 240 is generally similar to that of collimator 220 (FIGS. 9A and 9B), such that elements indicated by the same reference numerals in both collimators 220 and 240 are generally identical in construction and in operation. In collimator 240, each plate 222 is attached to a respective shaft 242, each shaft being rotatable by processor 28 so as to place its respective plate into, or out of, alignment with detectors 40. In one embodiment of the present invention, shafts 242 may be configured as a concentric set of shafts 244. By way of example, collimator 240 comprises three plates 222, and may be configured into three configurations. FIG. 10A illustrates a configuration with three plates 222 in alignment with detectors 40. FIG. 10B illustrates a configuration with one plate in alignment with the detectors, and two plates out of alignment.

Figure 11B:
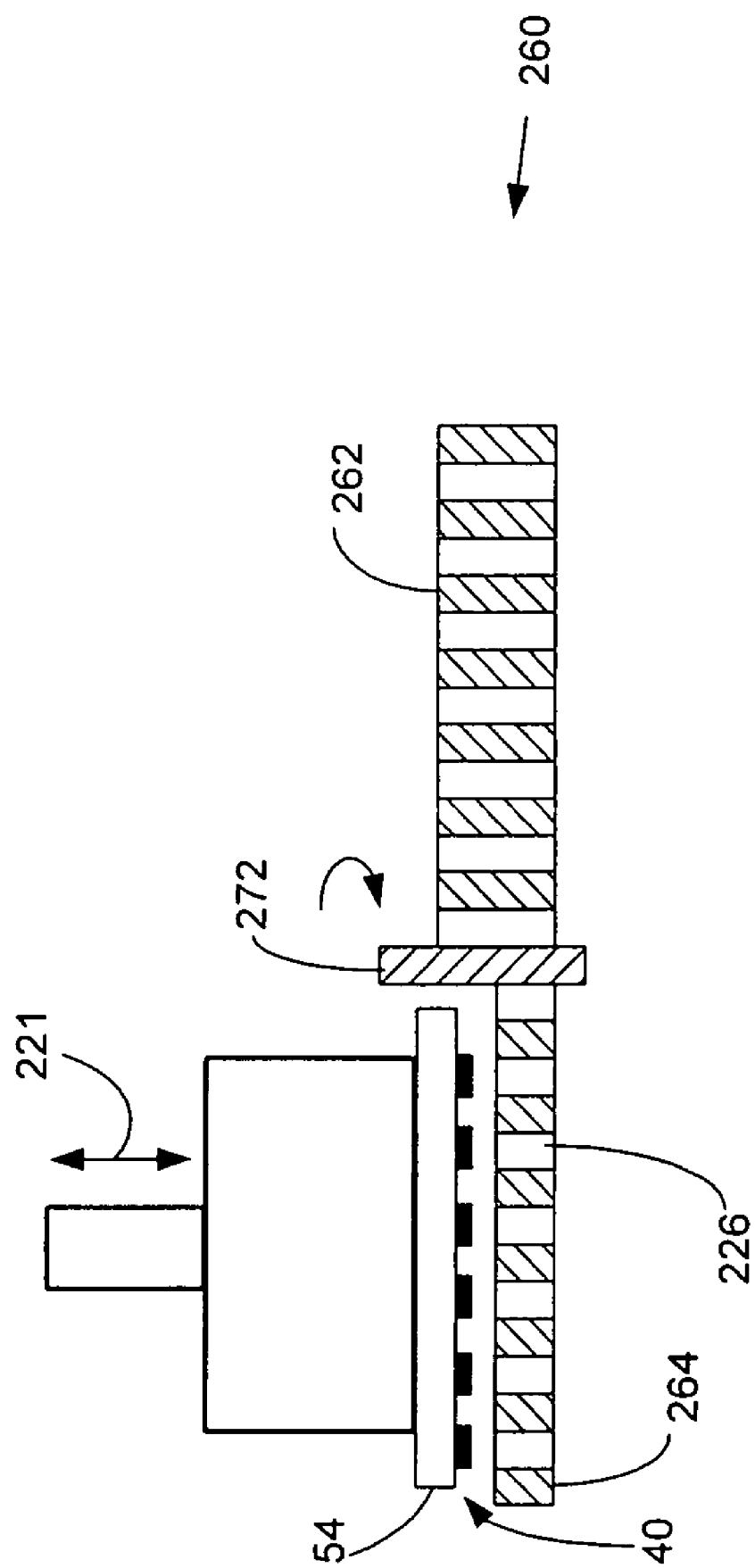

FIGS. 11A, 11B and 11C are schematic views of a collimator 260, according to an embodiment of the present invention. Apart from the differences described below, the operation of collimator 260 is generally similar to that of collimator 220 (FIGS. 9A and 9B), such that elements indicated by the same reference numerals in both collimators 220 and 260 are generally identical in construction and in operation. Collimator 260 comprises a plurality of collimator plates having different heights, rather than the same height collimator plates 222 in collimator 220. By way of example, collimator 260 comprises plates 262, 264, 266, and 268, herein referred to collectively as plates 270. Plates 270 have collimator channels 226 within the plates. Plates 270 are attached to a rotatable shaft 272, which is operated by processor 28. Processor 28 may rotate each of the plates so that channels 226 within one of the plates are in alignment with detectors 40, and so that the other channels are not aligned with the detectors.

FIG. 11A is a cross-sectional side view of a first configuration of collimator 260 showing plate 262 in alignment, and plate 264 out of alignment, with detectors 40. FIG. 11B is a cross-sectional side view of a second configuration of collimator 260 showing plate 264 in alignment, and plate 262 out of alignment, with detectors 40. In both configurations plates 266 and 268 (not shown in FIGS. 11A and 11B) are also out of alignment with detectors 40. Typically, detectors 40 may be raised or lowered, as explained above, so as to be at a substantially constant distance from the plate with which they are aligned with.

FIG. 11C shows a top view of collimator 260. For clarity, detectors 40, with which channels of one of plates 270 are aligned by processor 28, are not shown.

Collimator 260 may be positioned in four different configurations, corresponding to the four different heights of plates 270. Other embodiments similar to collimator 260, using different numbers of plates, each having a different height, will be apparent to those skilled in the art. All such embodiments are to be considered as being within the scope of the present invention.

Figure 12A:
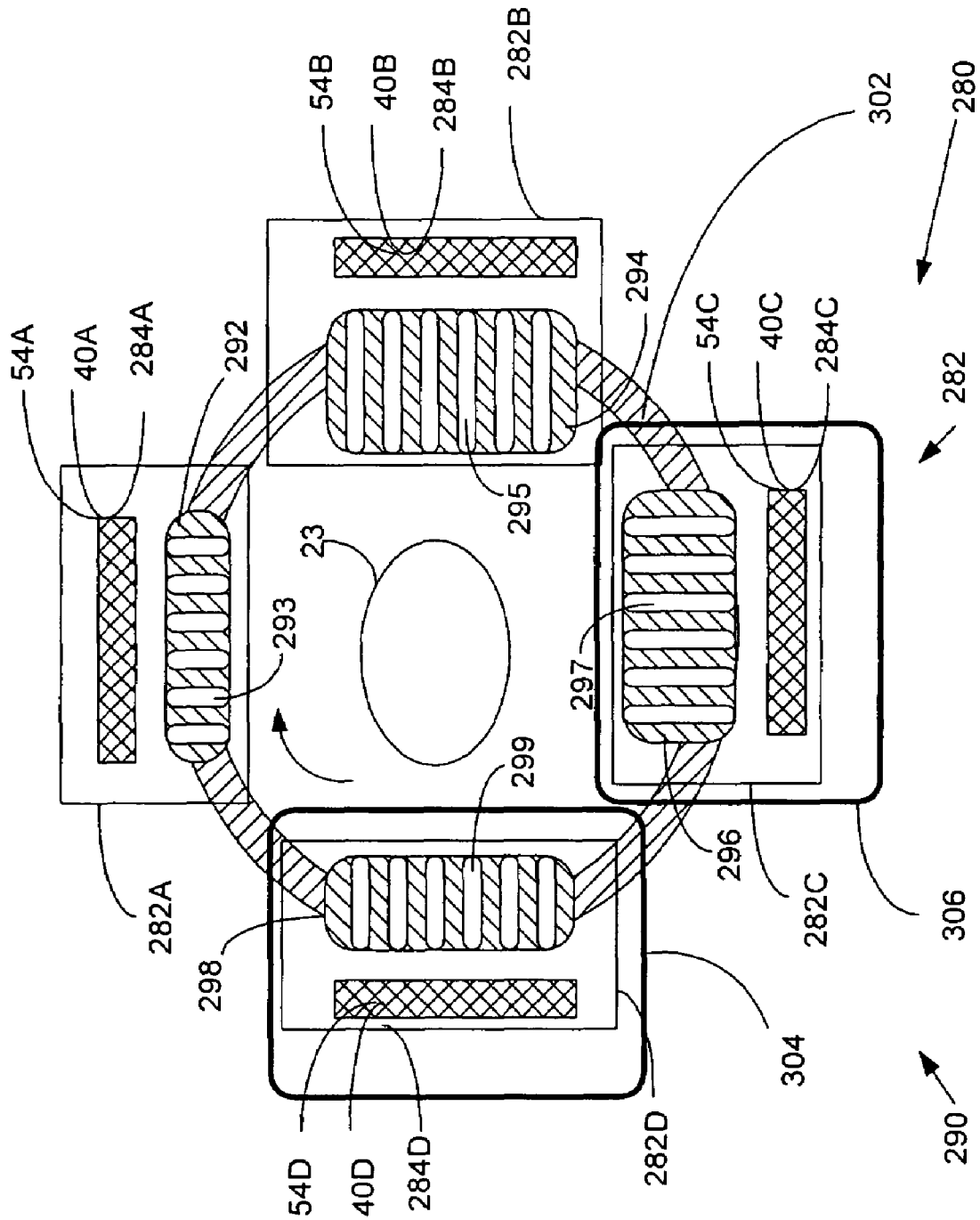
FIGS. 12A and 12B are schematic views of an alternative radiation detection system, according to an embodiment of the present invention.
Figure 12B:
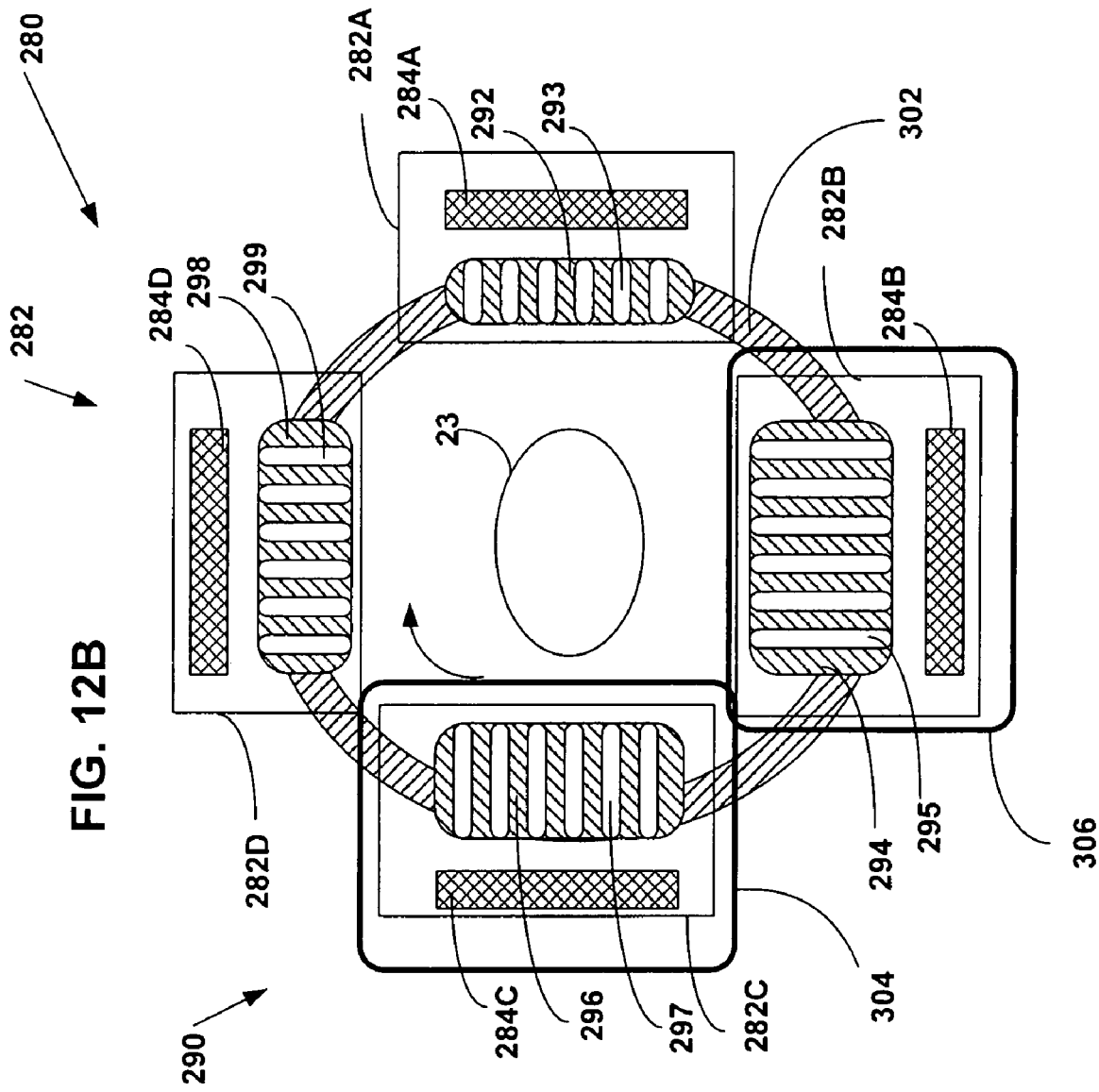

FIGS. 12A and 12B are schematic views of a radiation detection system 280, generally similar to a system used in Single Photon Counting Tomography (SPECT), according to an embodiment of the present invention. Unlike embodiments described above, system 280 comprises a plurality of generally similar camera heads 282, each camera head 282, except for the differences described below, being generally similar to camera head 24. Herein camera heads 282 are differentiated from each other with a letter suffix. By way of example, system 280 is assumed to comprise four camera heads 282A, 282B, 282C, and 282D. Each camera head 282 comprises a substantially similar detector mounting 54, each detector mounting 54 being associated with a set of detectors 40 to form a detector assembly 284. The detector mountings, detectors, and detector assemblies are differentiated from each other by having the same letter suffix as their respective camera heads.

Each set of detectors 40A, 40B, 40C, 40D is respectively associated with a different collimator 292, 294, 296, and 298, herein also referred to collectively as collimators 290. Each collimator 292, 294, 296, and 298 has respective channels 293, 295, 297 and 299 for their respective detectors. Collimators 290 are generally similar to plate 42 (FIG. 2). However, each collimator and its channels have a different length. Also, each collimator 290 is fixed with respect to its respective detectors.

Camera heads 282 are attached to a track 302, which acts as a positioning mount for the camera heads and is designed to allow all of the camera heads to be relocated in space to the same location 304. The camera heads and track are configured so that when the camera heads are in location 304, detectors 40A, 40B, 40C, and 40D are sequentially positioned in registration with each other. Also, when each camera head is in location 304, each collimator 290 is positioned with respect to its associated detectors 40 so that radiation from region 23 is directed by the channels of the collimator to the detectors. When a given camera head 282 is in location 304, processor 28 is configured to operate the camera head so as to receive signals from detectors 40.

System 280 thus effectively has a number of different configurations equal to the number of different camera heads 282 in the system. In the exemplary system illustrated in FIGS. 12A and 12B, system 280 has four configurations.

In some embodiments of system 280, processor 28 is configured to operate camera heads in one or more other locations defined by track 302. In some embodiments, camera heads in the multiple locations may be operated simultaneously. In each of the other locations, detectors 40 are in registration with each other and are positioned to receive radiation from region 23. For example, camera heads 282 and track 302 may be configured so that camera heads 282 may be positioned in registration, and operated by processor 28, in location 304 and in a second location 306.

In general, for systems such as system 280 comprising a plurality of camera heads, the number N of configurations of the system (where N is as defined above with respect to FIG. 5), is given by:

$$N = N_C \cdot N_L \quad (7)$$

where $N_C$ is the number of camera heads in the system, and $N_L$ is the number of locations in which each camera head may be positioned.

In an alternative arrangement of system 280, collimators 292, 294, 296, and 298 are not associated with a specific detector 40A, 40B, 40C, and 40D. In the alternative arrangement, detectors 40A, 40B, 40C, and 40D are typically fixed, and collimators 290 are movable into registration with the detectors using track 302. In a further alternative arrangement, collimators 292, 294, 296, and 298 may be coupled together to form, a common configurable collimator for detectors 40A, 40B, 40C, and 40D. Typically, in this further alternative configuration, track 302 rotates in steps into registration positions. The common configurable collimator is statically maintained in each, registration position for a time at least equal to a signal acquisition time for detectors 40A, 40B, 40C, and 40D. Thus track 302 moves in a rotational step motion between the acquisition static positions. In each rotational acquisition position the collimator between one of the detectors 40A-40D and the measured object has a different height. Accordingly, each detector 40A-40D has multiple acquisitions, each acquisition being performed by a configurable collimator that has different height for each of the different rotational acquisition positions.

In a yet further alternative arrangement of system 280, collimators 290 are each separately configurable with a plurality of dimensional configurations. For example, collimators 290 may be generally similar to collimator 26 (FIG. 2), but each collimator may be arranged to have different ranges of dimensional configurations. In another alternative arrangement of system 280, each collimator 290 may be generally similar to different types of collimators. For example, collimator 292 may be generally similar to collimator 26, and collimator 294 may be generally similar to a collimator 320 (described below).

FIGS. 13A, 13B, 13C and 13D are schematic diagrams of an alternate adjustable collimator 320, according to an embodiment of the present invention. Apart from the differences described below, the operation of collimator 320 is generally similar to that of collimator 26 (FIGS. 1 and 2), such that elements indicated by the same reference numerals in both collimators 26 and 320 are generally identical in construction and in operation. Collimator 320 comprises top plate 42 and a bottom plate 321. For clarity, in FIG. 13A only a section 323 of plate 42 and a section 324 of plate 321 are shown. In plate 42 channels 50 and detectors 40 are in alignment, as described with reference to collimator 26.

Figure 13A:
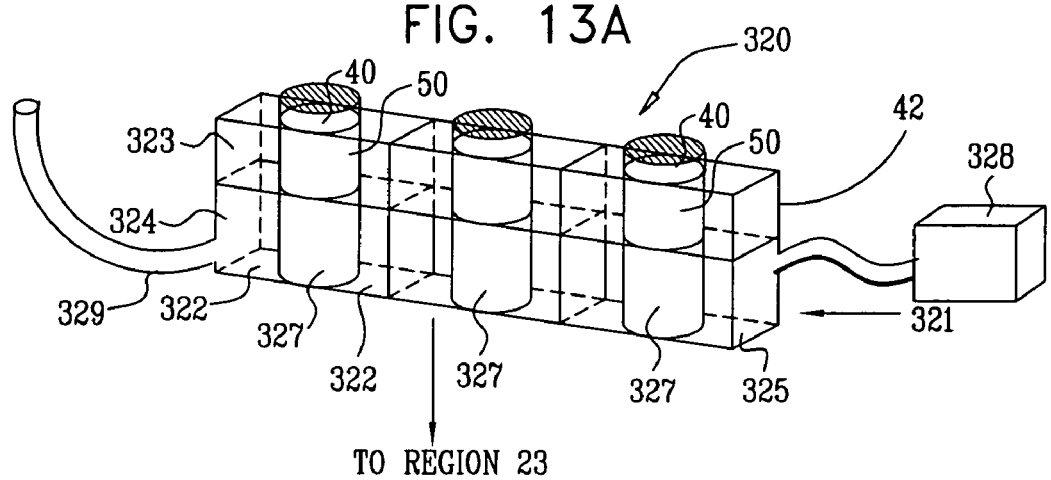
FIGS. 13A, 13B, 13C and 13D are schematic diagrams of a yet further alternative collimator, according to an embodiment of the present invention.
Figure 13C:
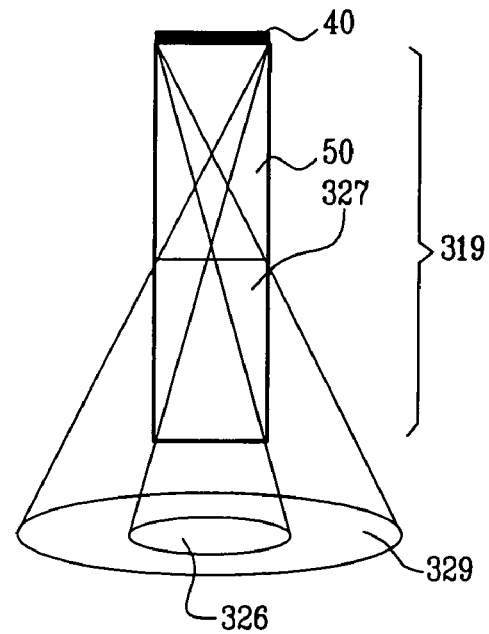
Figure 13D:
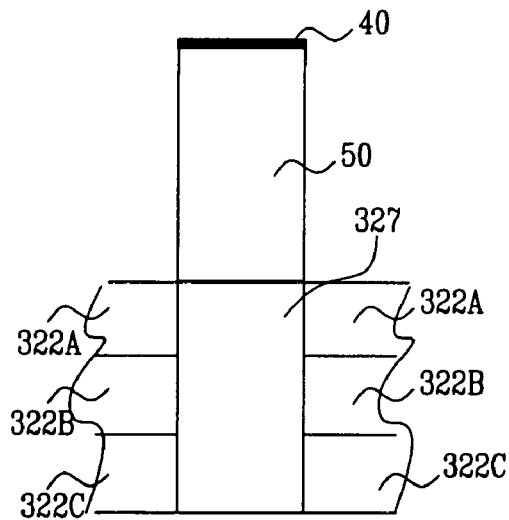
Figure 13B:
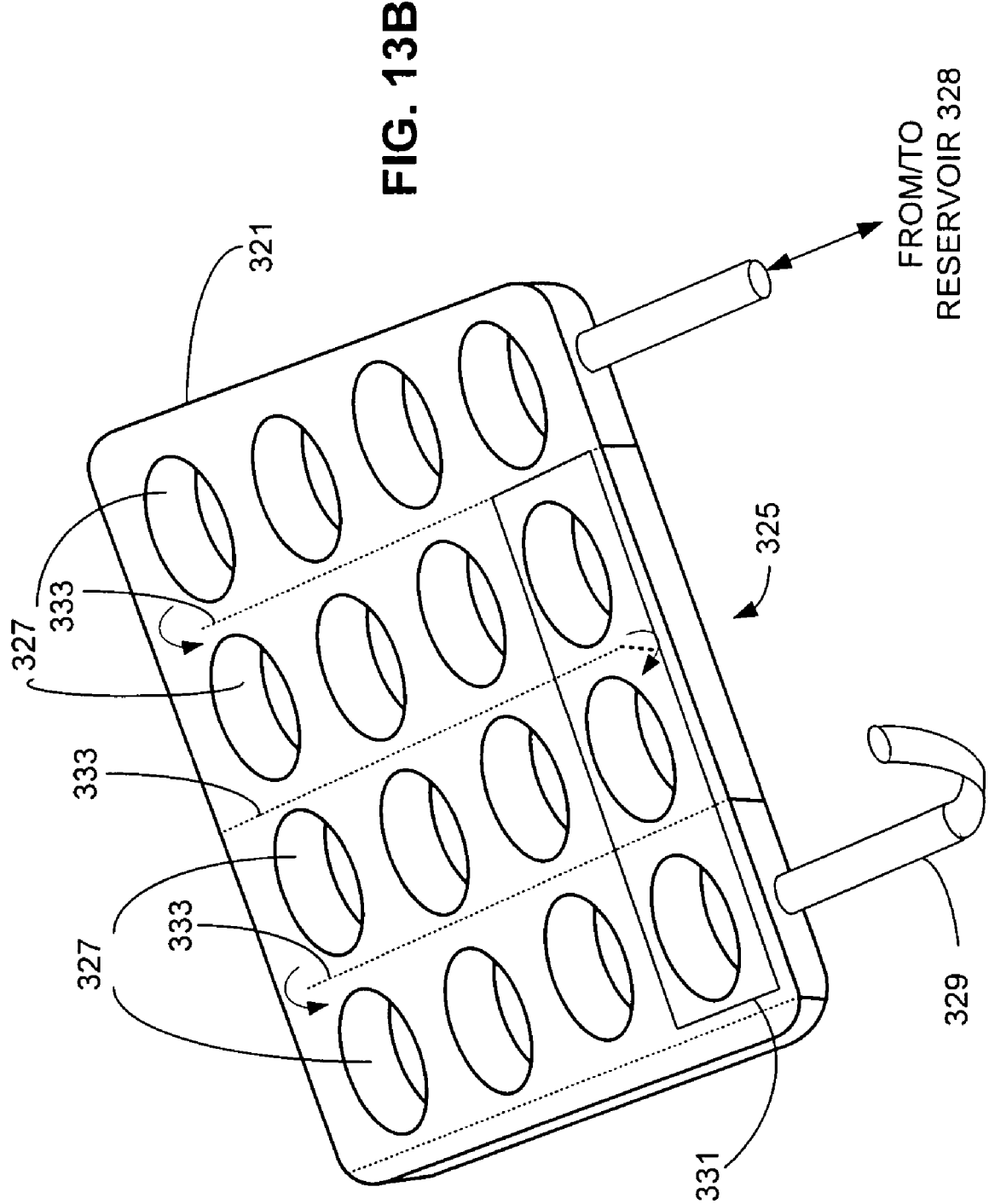

FIG. 13B is a schematic perspective view, of bottom plate 321. An outline 331 corresponds to section 324 illustrated in FIG. 13A. Bottom plate 321 faces region 23, and the plate comprises a cavity 322 and cylindrical channels 327 through the cavity. In contrast to plate 42, plate 321 is constructed from material, typically sheet material, which is substantially transparent to the radiation emitted from the radioisotopes in region 23.

Cavity 322 may be dynamically filled and/or emptied from a reservoir 328 with a liquid which is, relatively opaque to the radiation, such as mercury. Typically cavity 322 is divided internally with partitions 333 which guide the flow of the liquid, as shown by arrows in FIG. 13B. Reservoir 328 typically comprises a filling and discharge pump, and plate 321 comprises a vent 329 allowing air to leave/enter the cavity as it is filled/emptied. When empty, cavity 322 is transparent to the emitted radiation, and radiation reaches detector elements 40 through collimator channels 50. When cavity 322 is filled, the effective length of collimator 320 is extended to a bottom side 325 of plate 321, and collimator channels 327 act to direct radiation. Thus, when cavity 322 is filled, radiation reaches detectors 40 through channels 50 extended by corresponding channels 327 of bottom plate 321. In a disclosed embodiment, multiple plates generally similar to plate 321 may be stacked one on top of the other to form a collimator in which each plate can be filled/empty individually to produce a similar effect as that illustrated by FIGS. 9A and 9B, wherein plates 226 are aligned with/removed from detectors 40.

FIG. 13C is a cross-section through one pair of channels 50 and 327, which form an adjustable channel 319, and shows the effect that filling cavity 322 has on the radiation reaching detector 40. When cavity 322 is empty, corresponding to a first configuration, radiation passing through adjustable channel 319 subtends a large solid angle 329 at detector 40. When cavity 322 is filled, corresponding to a second configuration, radiation passing through adjustable channel 319 subtends a small solid angle 326 at the detector.

In some embodiments, cavity 322 may be partially filled so as to create different height channels 327, each height corresponding to a different configuration of collimator 320. Processor 28 may vary the heights in steps, or substantially continuously.

In some embodiments, only one filling point is used to fill cavity 322 from reservoir 328, although more filling points may be provided so that the cavity may be filled quickly.

Provided that cavity 322 is substantially completely filled, collimator 320 may be used in substantially any orientation.

FIG. 13D illustrates a cross-section of an alternative embodiment of collimator 320 wherein cavity 322 is subdivided, by way of example, into three isolated sub-compartments 322A, 322B, and 322C. Typically, the sub-compartments may be filled independently. Configuring cavity 322 to have isolated sub-compartments allows the cavity to be partially filled, while allowing collimator 320 to be used in non-horizontal orientations. Providing sub-compartments, and configuring the sub-compartments appropriately, also allows operator 32 to select different values for the solid angles and volumes of region 23 that are subtended by the different configurations, as well as increasing the number of configurations available in collimator 320. In collimator 320 the number of configurations depends on the number of sub-compartments, and the number of sub-compartments may be set to be any convenient number. In the example illustrated in FIG. 13D, there are three sub-compartments, and thus there are four configurations for collimator 320.

FIG. 14 is a schematic diagram of an adjustable collimator channel 430 formed in a cavity, according to an embodiment of the present invention. Apart from the differences described below, the operation, of adjustable collimator channel 430 is generally similar to that of adjustable collimator channel 47 (FIGS. 3A, 3B, 3C), such that elements indicated by the same reference numerals in collimator channels 47 and 430 are generally identical in construction and in operation. As opposed to adjustable collimator channel 47 described hereinabove, multiplicities of which are formed in two separate plates, multiplicities of adjustable collimator channels similar to adjustable collimator channel 430 may be formed in one plate 42. For clarity, FIG. 14 shows a section of plate 42 having only one adjustable collimator channel 430.

Channel 430 comprises a closed tubular cavity 432 formed in plate 42, the cavity having as its inner surface an inner cylinder 434 and as its outer surface an outer cylinder 435. Cylinder 434 is closed at its upper end by a given detector 40. An annulus 433, generally coplanar with detector 40, surrounds the detector and closes an upper end of cavity 432. Cavity 432 is closed at its lower end by an annulus 439. Cavity 432 has its outer surface an outer cylinder 436. Cavity 432 may be filled/emptied with a liquid which is opaque to radiation emitted by radioisotopes. The liquid is filled/emptied using a reservoir 428, which is generally similar to reservoir 328 (FIG. 13A). Cavity 432 has an opening (not shown) for inlet/outlet of air to/from the cavity.

Inner cylinder 434 and annulus 439 are selected from material substantially transparent to radiation. Thus, when cavity 432 is unfilled, a large solid angle defined by a lower edge 437 of cylinder 436 is subtended at detector 40. When cavity 432 is filled with liquid opaque to radiation, a smaller solid angle, defined by a lower edge 438 of cylinder 434, is subtended at detector 40. Cavity 432 being unfilled corresponds to a first dimensional configuration of collimator channel 430, cavity 432 being filled corresponds to a second dimensional configuration of the channel.

It will be understood that adjustments to collimator channel 430 are by changing a cross-sectional area of a channel forming the collimator and may be controlled by processor 28.

Although the embodiments described above typically relate to gamma ray detection in medical applications, detection of additional types of radiation may be performed, and may likewise be applied in the context of medical and/or non-medical applications, according to the principles of the present invention. Such types of radiation include electromagnetic radiation other than gamma rays, charged and uncharged particle radiation such as is generated from decay of radioisotopes, and radiation, such as ultrasound, transmitted as a wave motion by a material.

It will be appreciated that combinations of systems described above may be used to form collimators having multiple different configurations. For example, different configurations may be generated by varying an effective length and/or an effective cross-section of a channel.

It will thus be appreciated that, embodiments described above are cited by way of example, and that the present invention is not limited to what, has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Apparatus for imaging a body, comprising:
 a camera head positioned in a location and configured to detect radiation emitted from regions in the body so as to produce sliced images of radiation intensity emitted from a three dimensional structure of the regions, the camera head comprising:
   a two-dimensional array of D CdZnTe (CZT) detector elements, wherein D is an integer greater than 1, the array of D detector elements being defined by two orthogonal repetition vectors, the elements being mounted in the camera head and being respectively coupled to D electrodes, each electrode being configured to output signals indicative of intensities of radiation that are incident on a given detector element; and
   D adjustable collimators disposed respectively, in a collimator array defined by two orthogonal repetition vectors, in registration between the D detector elements and the body so as to define respective regions of the body from which the radiation emitted is incident on the detector elements, each of the adjustable collimators having N dimensional configurations defining different respective volumes of each of the regions, wherein N is an integer greater than 1, wherein each of the collimators is in registration with each of the detector elements so that the emitted radiation from the body traverses the collimators to impinge on the detector elements and wherein for each collimator the respective volumes of each of the regions have a respective common axis of symmetry which is normal to the two orthogonal repetition vectors, wherein each collimator comprises a respective different cavity which is configured to receive liquid opaque to the radiation; and
 a processor which is configured:
   to receive DN signals from the D electrodes corresponding to the respective volumes of each collimator while the camera head is in the location and while the respective common axis of symmetry of each collimator is fixed and while the adjustable collimators are in the N different dimensional configurations,
   to process the signals in order to form a three dimensional image of the body comprising a number of volume elements from which the radiation is emitted, and
   to produce sliced images of the three dimensional image while the two-dimensional array of CZT detector elements and the respective common axis of symmetry of each collimator are fixed with respect to the body, wherein the number of volume elements is a function of D and N.

2. The apparatus according to claim 1, wherein each collimator comprises a first collimator channel aligned with a second collimator channel and separated therefrom by an adjustable gap.

3. The apparatus according to claim 2, wherein the first collimator channel is aligned with one of the detector elements and is separated therefrom by a variable gap.

4. The apparatus according to claim 3, wherein the processor is coupled to adjust at least one of the variable gap and the adjustable gap.

5. The apparatus according to claim 2, wherein the first and second collimator channels comprise different cross-sectional areas.

6. The apparatus according to claim 1, wherein the liquid comprises mercury.

7. The apparatus according to claim 1, wherein each respective different cavity alters a length of each collimator on receipt of the liquid.

8. The apparatus according to claim 1, wherein each respective cavity comprises a different first cylinder and a different second cylinder having a different cross-section from the respective different first cylinder, and wherein each collimator on receipt of the liquid changes from the respective different first cylinder to the respective different second cylinder.

9. The apparatus according to claim 1, wherein the emitted radiation comprises gamma rays.

10. The apparatus according to claim 1, wherein the processor is configured to generate a representation of radioisotopes in the body in response to an intensity of the radiation.

11. The apparatus according to claim 1, wherein the processor is coupled to compute the number of the volume elements iteratively, so as to determine a largest number of the volume elements.

12. The apparatus according to claim 1, wherein the different respective volumes comprise respective first volumes and respective second volumes, and wherein the respective first volumes include the respective second volumes.

13. The apparatus according to claim 12, wherein the respective first volumes comprise respective first conic volumes, and wherein the respective second volumes comprise respective second conic volumes concentric with the respective first conic volumes.

14. The apparatus according to claim 1, wherein each respective different cavity comprises a plurality of isolated sub-compartments, each sub-compartment being independently filled with the liquid to form the N dimensional configuration, and so that each respective different cavity is operative in the N dimensional configurations in non-horizontal orientations.

15. The apparatus according to claim 1, wherein the volume elements are uniquely identifiable by an ordered triple (i, j, k) wherein i, j, k are positive integers having respective values $1, \ldots, I; 1, \ldots, J;$ and $1, \ldots, K;$ and wherein a number IJK of volume elements is a function of DN proportionality coefficients $\beta_{i,j,k}^{d,n}$ for each of the volume elements, wherein d, n are positive integers respectively identifying a particular detector element and a particular configuration of the adjustable collimators, d, n having respective values $1, \ldots, D;$ $1, \ldots N$, each proportionality coefficient being a ratio between the emitted radiation from a given volume element of the body and the radiation received by a given detector element for a respective collimator having a given dimensional configuration.

16. The apparatus according to claim 15, wherein $\beta_{i,j,k}^{d,n} = \alpha_{i,j,k}^{d,n} \cdot \theta_{i,j,k}^{d,n} \cdot V_{i,j,k}^{d,n}$
wherein:
$\alpha_{i,j,k}^{d,n}$ is an attenuation factor between volume element (i, j, k) and detector d in collimator dimensional configuration n, $\theta_{i,j,k}^{d,n}$ is a solid angle in which volume element (i, j, k) is viewed from detector d in collimator dimensional configuration n, and $V_{i,j,k}^{d,n}$ is a volume fraction of volume element (i, j, k) enclosed by the body as viewed from detector d in collimator dimensional configuration n.

17. The apparatus according to claim 16, wherein the processor is configured:
to calculate values of $\beta_{i,j,k}^{d,n}, \alpha_{i,j,k}^{d,n}, \theta_{i,j,k}^{d,n},$ and $V_{i,j,k}^{d,n}$ in response to geometrical relations between positions of the body, the D detector elements and the N dimensional configurations of the collimators, and wherein processing the signals comprises evaluating DN simultaneous linear equations:

$$S^{d,n} = \sum_{i,j,k} \alpha_{i,j,k}^{d,n} \cdot C_{i,j,k} \cdot \theta_{i,j,k}^{d,n} \cdot V_{i,j,k}^{d,n}$$

wherein $S^{d,n}$ is a total radiation intensity received by detector d in collimator configuration n, and
wherein $C_{i,j,k}$ is an average radioisotope concentration in volume element (i, j, k).

18. A method for imaging a body, comprising:
configuring a camera head to detect radiation emitted from regions in the body so as to produce sliced images of radiation intensity emitted from a three dimensional structure of the regions, the camera head comprising:
a two-dimensional array of D CdZnTe (CZT) detector elements, wherein D is an integer greater than 1, the array of D detector elements being defined by two orthogonal repetition vectors and being mounted in the camera head, the elements being respectively coupled to D electrodes, each electrode being configured to output signals indicative of intensities of radiation that are incident on a given detector element, and
D adjustable collimators respectively disposed, in a collimator array defined by the two orthogonal repetition vectors, in registration between the D detector elements and the body so as to define respective regions of the body from which the radiation emitted is incident on the detector elements, each of the adjustable collimators having N dimensional configurations defining different respective volumes of each of the regions, wherein N is an integer greater than 1, and wherein each of the collimators is in registration with each of the detector elements so that the emitted radiation from the body traverses the collimators to impinge on the detector elements, wherein for each collimator the respective volumes of each of the regions have a respective common axis of symmetry which is normal to the two orthogonal repetition vectors, and wherein each collimator comprises a respective different cavity which is configured to receive a liquid opaque to the radiation;
positioning the camera in a location;
receiving DN signals from the electrodes corresponding to the respective volumes of each collimator while the camera head is in the location and while the respective common axis of symmetry of each collimator is fixed and while the adjustable collimators are in the N different dimensional configuration;

processing the signals in order to form a three dimensional image of the body comprising a number of volume elements from which the radiation is emitted, wherein the number is a function of D and N; and producing sliced images of the three dimensional image while the two-dimensional array of CZT detector elements and the respective common axis of symmetry of each collimator are fixed with respect to the body.

19. The method according to claim 18, wherein each collimator comprises a first collimator channel aligned with a second collimator channel and separated therefrom by an adjustable gap.

20. The method according to claim 19, wherein the first collimator channel is aligned with one of the detector elements and is separated therefrom by a variable gap.

21. The method according to claim 20, and comprising adjusting at least one of the variable gap and the adjustable gap.

22. The method according to claim 19, wherein the first and second collimator channels comprise different cross-sectional areas.

23. The method according to claim 18, wherein the liquid comprises mercury.

24. The method according to claim 18, wherein each respective different cavity alters a length of each collimator on receipt of the liquid.

25. The method according to claim 18, wherein each respective different cavity comprises a respective different first cylinder and a respective different second cylinder having a different cross-section from the respective different first cylinder, and wherein on receipt of the liquid, each collimator changes from the respective different first cylinder to the respective different second cylinder.

26. The method according to claim 18, wherein the emitted radiation comprises gamma rays.

27. The method according to claim 18, and comprising generating a representation of radioisotopes in the body in response to an intensity of the radiation.

28. The method according to claim 18, wherein processing the signals comprises computing the number iteratively, so as to determine a largest number of the volume elements.

29. The method according to claim 18, wherein each respective different cavity comprises a plurality of isolated sub-compartments, each sub-compartment being independently filled with the liquid to form the N dimensional configurations, so that each respective different cavity is operative in the N dimensional configurations in non-horizontal orientations.

30. The method according to claim 18, wherein the different respective volumes comprise respective first volumes and respective second volumes, and wherein the respective first volumes include the respective second volumes.

31. The method according to claim 30, wherein the respective first volumes comprise respective first conic volumes, and wherein the respective second volumes comprise respective second conic volumes concentric with the respective first conic volumes.

32. The method according to claim 18, wherein the volume elements are uniquely identifiable by an ordered triple (i, j, k) wherein i, j, k are positive integers having respective values 1, ..., I; 1, ..., J; and 1, ..., K; and wherein a number IJK of volume elements is a function of DN proportionality coefficients $\beta_{i,j,k}^{d,n}$ for each of the volume elements, wherein d, n are positive integers respectively identifying a particular detector element and a particular configuration of the adjustable collimators, d, n having respective values 1, ..., D; 1, ... N, each proportionality coefficient being a ratio between the emitted radiation from a given volume element of the body and the radiation received by a given detector element for a respective collimator having a given dimensional configuration.

33. The method according to claim 32, wherein $\beta_{i,j,k}^{d,n} = \alpha_{i,j,k}^{d,n} \cdot \theta_{i,j,k}^{d,n} \cdot V_{i,j,k}^{d,n}$ wherein:

$\alpha_{i,j,k}^{d,n}$ is an attenuation factor between volume element (i, j, k) and detector d in collimator dimensional configuration n, $\theta_{i,j,k}^{d,n}$ is a solid angle in which volume element (i, j, k) is viewed from detector d in collimator dimensional configuration n, and $V_{i,j,k}^{d,n}$ is a volume fraction of volume element (i, j, k) enclosed by the body as viewed from detector d in collimator dimensional configuration n.

34. The method according to claim 33, and comprising:

calculating values of $\beta_{i,j,k}^{d,n}$, $\alpha_{i,j,k}^{d,n}$, $\theta_{i,j,k}^{d,n}$, and $V_{i,j,k}^{d,n}$ in response to geometrical relations between positions of the body, the D detector elements and the N dimensional configurations of the collimators, and wherein processing the signals comprises evaluating DN simultaneous linear equations:

$$S^{d,n} = \sum_{i,j,k} \alpha_{i,j,k}^{d,n} \cdot C_{i,j,k} \cdot \theta_{i,j,k}^{d,n} \cdot V_{i,j,k}^{d,n}$$

wherein $S^{d,n}$ is a total radiation intensity received by detector d in collimator configuration n, and wherein $C_{i,j,k}$ is an average radioisotope concentration in volume element (i, j, k).

* * * * *